(12) United States Patent
Ohlrogge et al.

(10) Patent No.: US 9,006,518 B2
(45) Date of Patent: Apr. 14, 2015

(54) F-BOX PROTEIN TARGETED PLANT OIL PRODUCTION

(75) Inventors: John B. Ohlrogge, Okemos, MI (US); Sari A. Ruuska, Turner ACT (AU); Yonghua Li, Aix-en-Provence (FR)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 13/039,018

(22) Filed: Mar. 2, 2011

(65) Prior Publication Data

US 2012/0017340 A1    Jan. 19, 2012

Related U.S. Application Data

(60) Continuation of application No. 12/609,562, filed on Oct. 30, 2009, now Pat. No. 7,915,480, which is a division of application No. 11/525,579, filed on Sep. 22, 2006, now abandoned.

(60) Provisional application No. 60/720,424, filed on Sep. 26, 2005.

(51) Int. Cl.
*A01H 5/10* (2006.01)
*C12N 15/82* (2006.01)
*C07H 21/04* (2006.01)
*C07K 14/415* (2006.01)

(52) U.S. Cl.
CPC .......... *C12N 15/8247* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 5,925,805 | A | 7/1999 | Ohlrogge et al. |
| 6,573,094 | B1 | 6/2003 | Harper et al. |
| 7,179,956 | B2 * | 2/2007 | Ravanello et al. ............ 800/281 |
| 7,915,480 | B2 | 3/2011 | Ohlrogge et al. |
| 2001/0034059 | A1 | 10/2001 | Allen et al. |
| 2003/0233670 | A1 | 12/2003 | Edgerton et al. |
| 2006/0107345 | A1 * | 5/2006 | Alexandrov et al. ......... 800/278 |
| 2006/0150283 | A1 * | 7/2006 | Alexandrov et al. ......... 800/288 |
| 2007/0143879 | A1 | 6/2007 | Ohlrogge et al. |
| 2011/0014706 | A2 * | 1/2011 | Cao et al. ..................... 435/419 |

FOREIGN PATENT DOCUMENTS

| | | |
|---|---|---|
| AU | 2006295375 | 9/2012 |
| CA | 2623720 C | 6/2014 |
| EP | 1033405 A2 * | 9/2000 |
| WO | WO-2005/103269 A2 | 11/2005 |

OTHER PUBLICATIONS

Heilmann et al. (PNAS, 101:10266-10271, 2004).*
Guo et al. (PNAS, 101: 9205-9210, 2004).*
Wells, Biochemistry 29:8509-8517, 1990.*
Keskin et al. (Protein Science, 13:1043-1055, 2004).*
Thornton et al. (Nature structural Biology, structural genomics supplement, Nov. 2000).*
Ngo et al., (The Protein Folding Problem and Tertiary Structure Prediction, K. Merz., and S. Le Grand (eds.) pp. 492-495,1994).*
Locus detail for gene At3g06240 from the *Arabidopsis* Information Resource, 2013 www(DOT)arabidopsis(DOT)org.*
"U.S. Appl. No. 12/609,562, Notice of Allowance mailed Nov. 24, 2010", 9 pgs.
"U.S. Appl. No. 12/609,562, Preliminary Amendment filed May 24, 2010", 4 pgs.
"U.S. Appl. No. 12/609,562, Preliminary Amendment filed Oct. 30, 2009", 9 pgs.
"Canadian Application Serial No. 2,623,720, Office Action mailed Oct. 12, 2012", 2 pgs.
"International Application Serial No. PCT/US2006/037111, International Preliminary Report on Patentability dated Mar. 26, 2008", 6 pgs.
"International Application Serial No. PCT/US2006/037111, International Search Report mailed Apr. 6, 2007", 3 pgs.
"International Application Serial No. PCT/US2006/037111, Written Opinion dated Mar. 26, 2008", 5 pgs.
"NCBI", [Online]. Retrieved From the Internet: <http://www.ncbi.nlm.nih.gov/entrez/viewer.fcgi?db~protein&val>, (Sep. 21, 2006), 16 pgs.
Andrade, M. A, et al., "A combination of the F-box motif and kelch repeats defines a large *Arabidopsis* family of F-box proteins", Plant Molecular Biology, vol. 46, (2001), 603-614.
Cernac, et al., "WRINKLED1 encodes an AP2/EREB domain protein involved in the control of storage compound biosynthesis in *Arabidopsis*", The Plant Journal: For Cell and Molecular Biology 40(4), (2004), 575-585.
Dharmasiri, N, et al., "Plant Development is Regulated by a Family of Auxin Receptor F Box Proteins", Developmental Cell, 9, (2005), 109-119.
Dharmasiri, N, et al., "The F-box protein TIR1 is an auxin receptor.", Nature, 435, (May 26, 2005), 441-445.
Francki, M, et al., "Wheat functional genomics and engineering crop improvement.", Genome Biology, 3(5), (2002), 1013.1-1013.5.
Gray, W M, et al., "Identification of an SCF ubiquitin-ligase complex required for auxin response in *Arabidopsis thaliana*.", Genes & Development, vol. 13, (1999), 1678-1691.
Hellman, H, et al., "Plant Development: Regulation by Protein Degradation.", Science, 297, (2002), 793-797.
Jako, C, et al., "Seed-Specific Over-Expression of an *Arabidopsis* CDNA Encoding a Diacylglycerol Acyltransferase Enhances Seed Oil Content and Seed Weight", Plant Physiology, 126(2), (2001), 861-874.
Kipreos, E T, et al., "The F-box protein family.", Genome Biology, vol. 1, No. 5, (/2000), 30021-3002.7.
Lai, Chia-Ping, et al., "Molecular Analyses of the *Arabidopsis* TUBBY-Like Protein Gene Family", Plant Physiology, 134, (Apr. 2004), 1586-1597.

(Continued)

*Primary Examiner* — Vinod Kumar
*Assistant Examiner* — Matthew Keogh
(74) *Attorney, Agent, or Firm* — Schwegman Lundberg & Woessner, P.A.

(57) ABSTRACT

Disclosed are genetic constructs, transgenic plant cells and transgenic plants, as well as associated methods, for increasing oil production in a plant using F-box gene sequences.

10 Claims, 18 Drawing Sheets

(56) References Cited

OTHER PUBLICATIONS

Larue, J, et al., "SCFGrr1_Mediated Ubiquitination of Gis4 Modulates Glucose Response in Yeast", J Mol. Bioi., vol. 349, (2005), 685-698.
Nemhauser, J, et al., "A New FronTIR in Targeted Protein Degradation and Plant Development", (2005), 970-972.
Roesler, K, et al., "Targeting of the *Arabidopsis* Homomeric Acetyl-Coenzyme a Carboxylase to Plastids of Rapeseeds.", Plant Physiology, vol. 113, No. 1, (1997), 75-81.
Thelen, J, et al., "Mertabolic Engineering of Fatty Acid Biosynthesis in Plants.", Metabolic Engineering, vol. 4, (2002), 12-21.
Voelker, et al., "Fatty Acid Bioscynthesis Redirected to Medium Chains in Transgenic Oilseed Plants.", Science, 257, (1992), 72-74.
Voelker, et al., "Genetic engineering of a quantitative trait: metabolic and genetic parameters influencing the accumulation of laurate in rapeseed.", The Plant Journal, 9(2), (1996), 229-241.
Zhang, J, et al., "From Laboratory to Field. Using Information from *Arabidopsis* to Engineer Salt, Cold, and Drought Tolerance in Crops.", Plant Physiology, 135, (2004), 615-621.
Zou, J T, et al., "Modification of See Oil Content and Acyl Composition in the *Brassicaceae* by Expression of a Yeast SN-2 Acyltransferase Gene.", Plant Cell., 9(6), (1997), 909-923.
"U.S. Appl. No. 11/525,579, Applicant's Summary of Examiner Interview filed Oct. 30, 2009", 1 pg.
"U.S. Appl. No. 11/525,579, Examiner Interview Summary mailed Oct. 19, 2009", 3 pgs.
"U.S. Appl. No. 11/525,579, Non Final Office Action mailed May 1, 2009", 29 pgs.
"U.S. Appl. No. 11/525,579, Non Final Office Action mailed Sep. 17, 2008", 27 pgs.
"U.S. Appl. No. 11/525,579, Response filed Jan. 21, 2009 to Non Final Office Action mailed Sep. 17, 2008", 24 pgs.
"U.S. Appl. No. 11/525,579, Response filed May 28, 2008 to Restriction Requirement mailed Apr. 28, 2008", 2 pgs.
"U.S. Appl. No. 11/525,579, Restriction Requirement mailed Apr. 28, 2008", 8 pgs.
"Australian Application Serial No. 2012216826, Preliminary Amendment filed Mar. 25, 2013", 4 pgs.
"Canadian Application Serial No. 2,623,720, Response filed Apr. 11, 2013 to Office Action mailed Oct. 12 2012", 10 pgs.
"Australian Application Serial No. 2012216826, First Examiner Report mailed Dec. 18, 2013", 3 pgs.
GenBank Accession No. AK1 18303.1, (Feb. 14, 2004).
"Australian Application Serial No.2012216826, Response filed Mar. 31, 2014 to First Examiner Report mailed Dec. 18, 2013", 11 pgs.
"Australian Application Serial No. 2012216826, Subsequent Examiners Report mailed May 1, 2014", 7 pgs.
Carninci, P., et al., "Balanced-size and long-size cloning of full-length, cap-trapped cDNAs into vectors of the novel lambda-FLC family allows enhanced gene discovery rate and functional analysis", Genomics, 77(1-2), (Sep. 2001), 79-90.

\* cited by examiner

POLYPEPTIDE SEQUENCE OF ARABIDOPSIS THALIANA F-BOX PROTEIN (GENBANK ACCESSION NO. NP_566277 (SEQ ID NO. 1))

```
  1 MKAIQLLWRA IMEATKRERR REDDDGEKAS PESLVLPPEI ITEILLRLPA KSIGRFRCVS
 61 KLFCTLSSDP GFAKIHLDLI LRNESVRSLH RKLIVSSHNL YSLDFNSIGD GIRDLAAVEH
121 NYPLKDDPSI FSEMIRNYVG DHLYDDRRVM LKLNAKSYRR NWVEIVGSSN GLVCISPGEG
181 AVFLYNPTTG DSKRLPENFR PKSVEYERDN FQTYGFGFDG LTDDYKLVKL VATSEDILDA
241 SVYSLKADSW RRICNLNYEH NDGSYTSGVH FNGAIHWVPT ESRHNQRVVV AFDIQTEEFR
301 EMPVPDEAED CSHRFSNFVV GSLNGRLCVV NSCYDVHDDI WVMSEYGEAK SWSRIRINLL
361 YRSMKPLCST KNDEEVLLEL DGDLVLYNFE TNASSNLGIC GVKLSDGFEA NTYVESLISP
421 NSYGIES
```

FIG. 10A

DNA SEQUENCE OF ARABIDOPSIS THALIANA F-BOX PROTEIN
(GENBANK ACCESSION NO. NM_111499 (SEQ ID NO. 2))

```
   1 TTTTTCAAAT CAAATCAGAA TACATTGATT CTGTATATCT TATTGAAAAA TCCATCAATT
  61 TACATCAACA ATTTTATATC TAATAATTAA TTTAAAGAGA AAATTTATAA AAGTTTATTA
 121 GAGCAAATAA CTCAAACTCG GATTTTATAG TCGTTATGAC CCGGTTTGAC TATTGAACCG
 181 TTTAACCGAG AAATTGGGAC TCAATTAAGA CAACCGAAAC TAGACCCGGA TCCAGTGTTA
 241 GCGGGCTAGA TTAAGGTGTC GGGTCATAGC GGAGAAGCAA CCAGACGCCA ACAATGAAAG
 301 CGATCCAGTT GCTGTGGGAA GCGATAATGG AGGCGACGAA GAGAGAAAGA CGGAGAGAAG
 361 ATGACGACGG CGAAAAAGCT TCACCGGAAT CACTCGTTCT TCCACCAGAG ATCATTACAG
 421 AAATTCTTCT CCGATTACCA GCCAAATCGA TCGGGCGATT CAGGTGCGTA TCAAAGCTCT
 481 TTTGCACTTT ATCGTCAGAT CCAGGGTTCG CGAAGATTCA CCTCGATCTG ATCCTTCGAA
 541 ACGAATCCGT AAGATCGCTC CACCGTAAGC TCATTGTGTC TTCACATAAT CTGTACTCGT
 601 TAGATTTCAA TTCGATCGGT GACGGAATTA GGGATTTAGC GGCTGTGGAA CACAATTATC
 661 CTCTTAAAGA CGATCCAAGC ATTTTCTCTG AGATGATTAG GAATTACGTG GGGGACCATC
 721 TGTACGATGA TCGTCGCGTG ATGCTTAAGC TGAATGCGAA ATCGTATCGA AGAAACTGGG
 781 TTGAGATCGT TGGATCTTCC AATGGTTTAG TGTGTATCTC TCCTGGTGAA GGAGCTGTTT
 841 TCTTGTATAA TCCAACTACC GGAGATTCCA AGAGATTACC TGAAAATTTT CGTCCCAAAT
 901 CTGTAGAATA CGAAAGAGAT AATTTCCAAA CTTATGGATT TGGTTTCGAT GGTCTCACTG
 961 ATGATTACAA ATTGGTGAAG CTTGTTGCTA CCAGTGAAGA TATTCTCGAT GCTAGTGTCT
1021 ATTCCTTGAA GGCTGACTCA TGGAGACGGA TCTGCAATTT GAATTATGAG CACAACGATG
1081 GCTCCTACAC GTCCGGTGTG CATTTCAACG GTGCGATTCA CTGGGTGTTC ACAGAGAGTA
1141 GGCACAACCA AAGAGTGGTT GTAGCATTTG ATATTCAAAC CGAGGAGTTT CGAGAGATGC
1201 CAGTGCCTGA TGAAGCTGAA GATTGTTCCC ATAGGTTTAG CAACTTTGTG GTCGGAAGTC
1261 TCAATGGACG TCTCTGTGTG GTCAATAGTT GCTACGATGT GCATGATGAT ATATGGGTGA
1321 TGAGTGAGTA CGGTGAAGCT AAATCCTGGA GCAGAATTCG AATCAACTTG TTGTATAGGT
1381 CGATGAAACC GCTCTGTTCG ACTAAGAACG ATGAAGAGGT TCTTCTGGAG CTTGATGGAG
1441 ACCTGGTGTT GTACAACTTT GAAACCAATG CATCGAGTAA TCTAGGAATT TGTGGGGTTA
1501 AGCTCAGTGA CGGGTTCGAG GCAAATACAT ACGTAGAGAG CCTCATATCA CCCAACTCTT
1561 ATGGTATAGA GAGCTGAGGA AGTCTGCTTT TTGCTAAGAT ATAATAAACC AACATTCGGA
1621 TTAGAAATGT TTTAGAAACA TAATCATGTA ATATGTATCA TGTAATTAAC AACGAATGGT
1681 CAATGGGTAT TTTAAGTTTC TTTCTCCT
```

FIG. 10B

FIG. 11 (SEQ ID NO: 6)

```
   1 ggccgcaaca gaggtggatg gacagacccg ttcttacacc ggactgggcg
  51 cgggatagga tattcagatt gggatgggat tgagcttaaa gccggcgctg
 101 agaccatgct caaggtaggc aatgtcctca gcgtcgagcc cggcatctat
 151 gtcgagggca ttggtggagc gcgcttcggg gataccgtgc ttgtaactga
 201 gaccggatat gaggccctca ctccgcttga tcttggcaaa gatatttgac
 251 gcattt atta gtatgtgtta attttcattt gcagtgcagt attttctatt
 301 cgatcttcat gtaattcgtt acaattaata aatattcaaa tcagattatt
 351 gactgtcatt tgtatcaaat cgtgtttaat ggatatttt attataatat
 401 tgatgatatc tcaatcaaaa cgtagataat aataatattt attaatatt
 451 tttgcgtcgc acagtgaaaa tctatatgag attacaaaat accgacaaca
 501 ttattcaaga tacatagaca ttaaccctga gactgttgga cagagctcat
 551 tggtacctca gatctgggta actggcctaa ctggccttgg aggagctggc
 601 aactcaaaat cccttt gcca aaaaccaaca tcatgccatc caccatgctt
 651 gtatccagct gcgcgcaatg taccccggcc tgtgtatccc aaagcctcat
 701 gcaacctaac agatggatcg ttggaaggc ctataacagc aaccacagac
 751 ttaaaaacctt gcgcctccat agacttaagc aaatgtgtgt acaatgtgga
 801 tcctaggccc aacctttgat gcctatgtga cacgtaaaca gtactctcaa
 851 ctgtccaatc gtaagcgttc ctagccttcc agggcccagc gtaagcaata
 901 ccagccacaa caccctcaac ctcagcaacc aaccaagggt atctacttg
 951 caacctctct agatcatcaa tccactcttg tggtgttgt ggctctgtcc
1001 taaagttcac tgtagacgtc tcaatgtaat ggttaacgat atcacaaacc
1051 gcggccatat cagctgctgt agctggccta atctcaactg gtctcctctc
1101 cggagaagcc atggtttgga tccacaaact tacaaatttc tctgaagttg
1151 tatcctcagt acttcaaaga aaatagctta caccaattct ttctgtttt
1201 cacaaatgcc gaacttggtt ccttatatag gaaaactcaa gggcaaaaat
1251 gacacggaaa aatatataaag gataagtagt gggggataag attccttttgt
1301 gataaggtta cttccgccc ttacattttc caccttacat gtgtcctcta
1351 tgtctctttc acaatcaccg accttatctt ctctttttca ttgttgtcgt
1401 cagtgcttac gtcttcaaga ttcttttctt cgcctggttc ttcttttca
1451 atttctacgt attcttcttc gtattctggc agtataggat cttgtatctg
1501 tacattcttc atttttgaac ataggttgca tatgtgccgc atattgatct
1551 gcttcttgct gagctcacat aatacttcca tagttttttcc cgtaaacatt
1601 ggattcttga tgctacatct tggataatta cctctggcc ggcgcgaat
1651 tcgttggtag ggtgctagga aacttgtttt tggggtttg tataagggtt
1701 gaaacatccc tgaagtgtct catttatt tatttattct ttgctgataa
1751 aaaaataaaa taaagaagc taagcacacg gtcaaccatt gctctactgc
1801 taaaagggtt atgtgtagtg tttactgca taattatgc agcaaacaag
1851 acaactcaaa ttaaaaaatt tcctttgctt gttttttgt tgtctctgac
1901 ttgacttctt tgtggaagtt ggttgtaaa ggattgggac accattgtcc
1951 ttcttaattt aattttattc tttgctgata aaaaaaaaa attcatata
2001 gtgttaaata ataatttgtt aaataaccaa aaagtcaaat atgttcactc
2051 tcgtttaaat aattgagatt cgttccagca aggctaaacg attgtataga
2101 cttatgacaa tatttacttt tttatagata aatgttatat tataataaat
2151 ttatatacat atattatatg ttatttatta ttattatta tttcaaatcc
2201 ttcaatattt tatccaacca actcataatt tttttttat ctgtaagaag
2251 caataaaatt aaatagaccc acttaagga tgatccaacc tttatacaga
2301 gtaagagagt tcaaatagta cctttcata tacatatcaa ctaaaatatt
2351 agaaatatca tggatcaaac cttataaaga cattaaataa gtggataagt
2401 ataatatata aatgggtagt atataatata aaatggata caaacttctc
2451 tctttatat tgttatgct ccttaacatc ctaatataat acataagtgg
2501 gtaatatata atatataat ggagacaaac ttcttccatt ataattgtta
2551 tgtcttctta acacttatgt ctcgttcaca atgctaaagt tagaattgtt
```

```
2601  tagaaagtct tatagtacac attttgttttct gtactatttg aagcattcca
2651  taagccgtca cgattcagat gatttataat aataagagga aatttatcat
2701  agaacaataa ggtgcataga tagagtgtta atatatcata acatccttttg
2751  tttattcata gaagaagtga gatggagctc agttattata ctgttacatg
2801  gtcggataca atattccatg ctctccatga gctcttacac ctacatgcat
2851  tttagttcat actggtgacc ctcgaggcga tcgctttggc cggccattta
2901  aatggcgcgc cttgcccgg gcttttcctgc agggtttATC AACCACTTTG
2951  TACAAGAAAG CTGAACGAGA AACGTAAAAT GATATAAATA TCAATATATT
3001  AAATTAGATT TTGCATAAAA AACAGACTAC ATAATACTGT AAAACACAAC
3051  ATATCCAGTC ACTATGGTCG ACCTGCAGAC TGGCTGTGTA TAAGCGAGCC
3101  TCACATTTAT ATTCCCAGA ACATCAGGTT AATGGCGTTT TTGATGTCAT
3151  TTTCGCGGTG GCTGAGATCA GCCACTTCTT CCCCGATAAC GGACACCGGC
3201  ACACTGGCCA TATCGGTGGT CATCATGCGC CAGCTTTCAT CCCCGATATG
3251  CACCACCGGG TAAAGTTCAC GGGAGACTTT ATCTGACAGC AGACGTGCAC
3301  TGGCCAGGGG GATCACCATC CGTCGCCCGG GCGTGTCAAT AATATCACTC
3351  TGTACATCCA CAAACAGACG ATAACGGCTC TCTCTTTTAT AGGTGTAAAC
3401  CTTAAACTGC ATTCACCAG TCCTGTTCT CGTCAGCAAA AGAGCCGTTC
3451  ATTTCAATAA ACCGGGCGAC CTCAGCCATC CCTTCCTGAT TTTCCGCTTT
3501  CCAGCGTTCG GCACGCAGAC GACGGGCTTC ATTCTGCATG GTTGTGCTTA
3551  CCAGACCGGA GATATTGACA TCATATATGC CTTGAGCAAC TGATAGCTGT
3601  CGCTGTCAAC TGTCACTGTA ATACGCTGCT TCATAGCACA CCTCTTTTTG
3651  ACATACTTCG GGTATACATA TCAGTATATA TTCTTATACC GCAAAAATCA
3701  GCGCGCAAAT ACGCATACTG TTATCTGGCT TTTAGTAAGC CGGATCCAGA
3751  TCTTTACGCC CCGCCCTGCC ACTCATCGCA GTACTGTTGT AATTCATTAA
3801  GCATTCTGCC GACATGGAAG CCATCACAGA CGGCATGATG AACCTGAATC
3851  GCCAGCGGCA TCAGCACCTT GTCGCCTTGC GTATAATATT TGCCCATGGT
3901  GAAAACGGGG GCGAAGAAGT TGTCCATATT GGCCACGTTT AAATCAAAAC
3951  TGGTGAAACT CACCCAGGGA TTGGCTGAGA CGAAAAACAT ATTCTCAATA
4001  AACCCTTTAG GGAAATAGGC CAGGTTTTCA CCGTAACACG CCACATCTTG
4051  CGAATATATG TGTAGAAACT GCCGGAAATC GTCGTGGTAT TCACTCCAGA
4101  GCGATGAAAA CGTTTCAGTT TGCTCATGGA AAACGGTGTA ACAAGGGTGA
4151  ACACTATCCC ATATCACCAG CTCACCGTCT TTCATTGCCA TACGGAATTC
4201  CGGATGAGCA TTCATCAGGC GGGCAAGAAT GTGAATAAAG GCCGGATAAA
4251  ACTTGTGCTT ATTTTTCTTT ACGGTCTTTA AAAAGGCCGT AATATCCAGC
4301  TGAACGGTCT GGTTATAGGT ACATTGAGCA ACTGACTGAA ATGCCTCAAA
4351  ATGTTCTTTA CGATGCCATT GGGATATATC AACGGTGGTA TATCCAGTGA
4401  TTTTTTTCTC CATTTTAGCT TCCTTAGCTC CTGAAAATCT CGCCGGATCC
4451  TAACTCAAAA TCCACACATT ATACGAGCCG GAAGCATAAA GTGTAAAGCC
4501  TGGGGTGCCT AATGCGGCCG CCATAGTGAC TGGATATGTT GTGTTTTACA
4551  GTATTATGTA GTCTGTTTTT TATGCAAAAT CTAATTTAAT ATATTGATAT
4601  TTATATCATT TTACGTTTCT CGTTCAGCTT TTTTGTACAA ACTTGTTGAT
4651  aaacttaatt aaggatccta gagtagtatt gaatatgagt tgggttgggg
4701  tattatagta gtagagtagt agtactctgg atggatggat gatgaaagaa
4751  gtgagtgata ttagaggtat ttataggtat tatataagag agaaggtggt
4801  tggaacatgc atggagattt gggcatggga tgacacgcat atgcaggttg
4851  acgtgtgttg aagtgaagaa attgaggtgg cggaagagaa tgaatatata
4901  caggtggttg tggtgatgat gaagaaaaag gcaatgtgtt tgtgtgtggg
4951  ttgagatggg tgagccattt aaagtgcatg ttaagcacgt gttgctttgc
5001  atggcattta gacatacatg gacgcggcga tcttgatcag ccagtgacta
5051  attgagttg gttgtgtgat tgcgtttgt ctctctgttt tgtcttttt
5101  ctttgttctc tgtcttttc ttgcgcaagc atccatgcat gaaccaaaag
5151  accacagagt gtcatggcaa ccacagtaa ttccagttac ggacttacat
5201  accaagaaaa ggtaaagca ataagaaata tatgaaaatt agtccaccat
5251  aaatcttata gtttatggtt tagggtaaca ctctaacact ctactacatt
5301  acttatattt acttaaact atcataaaa caatttaaac atagtagaat
5351  aataaatcaa tagtcacaaa ttcaacaatt aaacttaaaa ttaaaaagt
5401  aatatttaa ttatatctaa ttaatttttt agaagtaata ttgagtattt
```

FIG.11 (cont'd)

```
5451  gatatatgaa atcttgaata tagtaactat tattaaaatt actttagaag
5501  atgtgtctcg catgtaaaag cagatcttca gttacttccg tagtgtcaaa
5551  tgggaattat agaattttgc ataacatgac ttgcttcaga aataccacaa
5601  atcattgttt ggtgaaattt tcattgtata aaaaaaatac aatgataatt
5651  ggattttttt attcaaagaa aaaaatggct agttgtgtca ctgggtgttg
5701  ctttaagatc agtcgaataa aaaaattatg gagttaaatt ttattacttt
5751  tgaaacaact tatrattatg agatttacgt ggttgaaaaa tatttgataa
5801  atatatttt aaaatataaa atgggaaatc cttcttaagg taaagaattt
5851  gtttatattg tatattaaac acttatatga agaagaataa gaataaatca
5901  ttatgcttc taccaacgct aaaattaagt aaattatata tttcaatatg
5951  aaaatgttag actacattaa agatagacgg gacttcataa aattttatgc
6001  ggtttgaaaa tgtttaacaa ataataaatt tgtagggata tcgtgtgcgg
6051  aagcgtgata atttcaacca aagattatga gaaattaaag taacaagtaa
6101  agtgagaatg ataccagaat tttaggtgg aaaacccctt taaatagagg
6151  taaaaaacca ccggcgagag agccaaaact ttcactataa tgatactggg
6201  agtacaatgg cggccggggc tgcaattgat ccggtgagta atattgtacg
6251  gctaagagcg aatttggcct gtagacctca attgcgagct ttctaattc
6301  aaactattcg ggcctaactt ttggtgtgat gatgctgact ggcaggatat
6351  ataccgtcgt aatttgagct cgtgtgaata agtcgctgtg tatgtttgtt
6401  tgattgtttc tgttggagtg cagcccattt cacggacaa gtcggctaga
6451  ttgatttagc cctgatgaac tgccgagggg aagccatctt gagcgcggaa
6501  tgggaatgga tcgaaccggg agcacaggat gacgcctaac aattcattca
6551  agccgacacc gcttcgcggc gcggttaat tcaggagtta aacatcatga
6601  gggaagcggt gatcgccgaa gtatcgactc aactatcaga ggtagttggc
6651  gtcatcgagc gccatctcga accgacgttg ctggccgtac atttgtacgg
6701  ctccgcagtg gatggcggcc tgaagccaca cagtgatatt gatttgctgg
6751  ttacggtgac cgtaaggctt gatgaaacaa cgcggcgagc tttgatcaac
6801  gaccttttgg aaacttcggc ttccctgga gagagcgaga ttctccggc
6851  tgtagaagtc accattgttg tgcacgacga catcattccg tggcgttatc
6901  cagctaagcg cgaactgcaa tttggagaat ggcagcgcaa tgacattctt
6951  gcaggtatct tcgagccagc cacgatcgac attgatctgg ctatcttgct
7001  gacaaaagca agagaacata gcgttgcctt ggtaggtcca gcggcggagg
7051  aactctttga tccggttcct gaacaggatc tatttgaggc gctaaatgaa
7101  accttaacgc tatggaactc gccgcccgac tgggctggcg atgagcgaaa
7151  tgtagtgctt acgttgtccc gcattcggta cagcgcagta accggcaaaa
7201  tcgcgccgaa ggatgtcgct gccgactggg caatggagcg cctgccggcc
7251  cagtatcagc ccgtcatact tgaagctagg caggcttatc ttggacaaga
7301  agatcgcttg gcctcgcgcg cagatcagtt ggaagaattt gtccactacg
7351  tgaaaggcga gatcaccaag gtagtcggca aataatgtct aacaattcgt
7401  tcaagccgac gccgcttcgc ggcgcggctt aaccaagcg ttagagagct
7451  gggaagact atgcgcgatc tgttgaaggt ggttctaagc ctcgtacttg
7501  cgatggcatt tcgatcgaaa ggggtacaaa ttccactaa gcgctcgggg
7551  gctgagaaag cccagtaagg aaacaactgt aggttcgagt cgcgagatcc
7601  ccggaacca aaggaagtag gttaaacccg ctccgatcag gccgaggccac
7651  gccaggccga gaacattggt tcctgtaggc atgggatgg gcggatcaaa
7701  cactaaagct actggaacga gcagaagtcc tccggcgcc agttgccagg
7751  ccgtaaaggt gagcagaggc acgggaggtt gccacttgcc ggtcagcacg
7801  gttccgaacg ccatggaaac cgccccgcc aggccgctg cgacgccgac
7851  aggatctagc gctgcgtttg gtgtcaacac caacagcgcc acgcccgcag
7901  ttccgcaaat agccccagg accgccatca atcgtatcgg gctacctagc
7951  agagcggcag agatgaacac gaccatcagc ggctgaacag cgcctaccgt
8001  cgccgcgacc cgccggcag gcggtagacc gaaataaaca acaagctcca
8051  gaatagcgaa atattaagtg cgccgaggat gaagatgcgc atccaccaga
8101  ttccgtggg aatctgtcgg acgatcatca cgagcaataa accgccggc
8151  aacgcccgca gcagcatacc gggcaccct cggctcgct gttcgggctc
8201  cacgaaaacg ccggacagat gcgcttgtg agcgtccttg gggccgtcct
8251  cctgtttgaa gaccgacagc caatgatct cgccgtcgat gtaggcgccg
```

FIG.11 (cont'd)

```
8301  aatgccacgg catctgcaa ccgttcagcg aacgcctcca tgggcttttt
8351  ctcctcgtgc tcgtaaacgg acccgaacat ctctggagct ttcttcaggg
8401  ccgacaatcg gatctcgcgg aaatcctgca cgtcggccgc tccaagccgt
8451  cgaatctgag ccttaatcac aattgtcaat tttaatcctc tgttttatcgg
8501  cagttcgtag agcgcgccgt gcgccgagc gatactgagc gaagcaagtg
8551  cgtcgagcag tgcccgcttg ttcctgaaat gccagtaaag cgctggctgc
8601  tgaaccccca gccggaactg accccacaag gccctagcgt ttgcaatgca
8651  ccaggtcatc attgacccag gcgtgttcca ccaggccgct gcctcgcaac
8701  tcttcgcagg cttcgccgac ctgctcgcgc cacttcttca cgcgggtgga
8751  atccgatccg cacatgaggc ggaaggtttc cagcttgagc gggtacggct
8801  cccggtgcga gctgaaatag tcgaacatcc gtcgggccgt cggcgacagc
8851  ttgcggtact tctcccatat gaatttcgtg tagtggtcgc cagcaaacag
8901  cacgacgatt tcctcgtcga tcaggacctg gcaacgggac gttttcttgc
8951  cacggtccag gacgcggaag cggtgcagca gcgacaccga ttccaggtgc
9001  ccaacgcggt cggacgtgaa gcccatcgcc gtcgcctgta gggcgacag
9051  gcattcctcg gcttcgtgt aataccggcc attgatcgac cagcccaggt
9101  cctggcaaag ctcgtagaac gtgaaggtga tcggctcgcc gatagggtg
9151  cgcttcgcgt actccaacac ctgctgccac accagttcgt catcgtcggc
9201  ccgcagctcg acgccggtgt aggtgatctt cacgtccttg ttgacgtgga
9251  aaatgaccct gttttgcagc gcctcgcgcg ggattttctt gttgcgcgtg
9301  gtgaacaggg cagagcgggc cgtgtcgttt ggcatcgctc gcatcgtgtc
9351  cggccacggc gcaatatcga acaaggaaag ctgcattttcc ttgatctgct
9401  gcttcgtgtg tttcagcaac gcggctgct tggcctcgct gacctgtttt
9451  gccaggtcct cgccggcggt tttttcgctc ttggtcgtca tagttcctcg
9501  cgtgtcgatg gtcatcgact tcgccaaacc tgccgcctcc tgttcgagac
9551  gacgcgaacg ctccacggcg gccgatgcg cgggcagggc aggggagcc
9601  agttcacgc tgtcgcgtc gatcttggcc gtagcttgct ggaccatcga
9651  gccgacggac tggaaggttt cgcggggcgc acgcatgacg gtgcggcttg
9701  cgatggtttc ggcatcctcg gcggaaaacc ccgcgtcgat cagttcttgc
9751  ctgtatgcct tccggtcaaa cgtccgattc attcaccctc cttgcgggat
9801  tgccccgact cacgcgggg caatgtgcc ttattcctga tttgaccgc
9851  ctggtgcctt ggtgtcaaga taatccacct tatcggcaat gaagtcggtc
9901  ccgtagaccg tctggccgtc cttctcgtac ttggtattcc gaatcttgcc
9951  ctgcacgaat accagcgacc ccttgccaa atacttgccg tgggcctcgg
10001 cctgagagcc aaaacacttg atgcggaaga agtcggtgcg ctcctgcttg
10051 tcgccggcat cgttgcgcca ctcttcatta accgctaatt cgaaaattgc
10101 ttgccgcttg ttagaattgc catgacgtac ctcggtgtca cgggtaagat
10151 taccgataaa ctggaactga ttatggcnnc tcgaaattcc ctccggtcttg
10201 ccttgctcgt cggtgatgta cttcaccagc tccgcgaagt cgctcttctt
10251 gatggagcgc atggggacgt gcttggcaat cacgcgcacc cccggccgt
10301 tttagcggct aaaaagtca tggctctgcc ctcgggcgga ccacgcccat
10351 catgaccttg ccaagctcgt cctgcttctc ttcgatcttc gccagcaggg
10401 cgaggatcgt ggcatcaccg aaccgcgccg tgcgcgggtc gtcggtgagc
10451 cagagtttca gcaggccgcc caggcggccc aggtcgccat tgatcgggc
10501 cagctcgcgg acgtgctcat agtccacgac gcccgtgatt ttgtagccct
10551 ggcgacggc cagcaggtag gcgacaggc tcatgccggc cgccgccgcc
10601 ttttcctcaa tcgtctcttcg ttcgtctgga aggcagtaca ccttgatagg
10651 tgggctgccc ttcctggttg gcttggtttc atcagccatc cgcttgccct
10701 catctgttac gccggcgta gccggccagc ctgcagagc aggattcccg
10751 ttgagcaccg ccaggtgcga ataagggaca gtgaagaagg aacacccgct
10801 cgcgggtggg cctacttcac ctatcctgcc cggctgacgc cgttggatac
10851 accaaggaaa gtctacacga acccttggc aaaatcctgt atatcgtgcg
10901 aaaaggatg gatatacgca aaaaatcgct ataatgaccc cgaagcaggg
10951 ttatgcagcg gaaaagatcc gtcgaccctt tcgacgctc accgggctgg
11001 ttgccctgcc cgctgggctg gcggccgtct atggcctgc aaacgcgcca
11051 gaaacgccgt cgaagccgtg tgcgagacac cgcggccgcc gggtttgtgg
11101 ataccacgcg gaaaacttgg ccctcactga cagatgaggg gcggacgttg
```

FIG. 11 (cont'd)

```
11151  acacttgagg  ggccgactca  cccggcgcgg  cgttgacaga  tgaggggcag
11201  gctcgatttc  ggccggcgac  gtggagctgg  ccagcctcgc  aaatcggcga
11251  aaacgcctga  ttttacgcga  gtttcccaca  gatgatgtgg  acaagcctgg
11301  ggataagtgc  cctgcggtat  tgacacttga  ggggcgcgac  tactgacaga
11351  tgaggggcgc  gatccttgac  acttgagggg  cagagtgatg  acagatgagg
11401  ggcgcaccta  ttgacatttg  aggggctgtc  cacaggcaga  aaatccagca
11451  tttgcaaggg  tctccgcccg  ttttttcggcc  accgctaacc  tgtcttttaa
11501  cctgcttttta  aaccaatatt  tataaacctt  gttttttaacc  agggctgcgc
11551  cctggcgcgt  gaccgcgcac  gccgaagggg  ggtgcccccc  cttctcgaac
11601  cctccggcc  cgctaacgcg  ggcctcccat  cccccaggg  gctgcgcccc
11651  tggccgcga  acggcctcac  cccaaaaatg  gcaggccaag  cttgcttggt
11701  cgttccggta  cgtaccgtga  acgtcggctc  gattgtacct  gcgttcaaat
11751  actttgcgat  cgtgttgcgc  gcctgccgg  tgcgtcggct  gatctcacgg
11801  atcgactgct  tctctcgcaa  cgccatccga  cggatgatgt  ttaaaagtcc
11851  catgtggatc  actccgttgc  cccgtcgctc  accgtgttgg  ggggaaggtg
11901  cacatggctc  agttctcaat  ggaaattatc  tgcctaaccg  gctcagttct
11951  gcgtagaaac  caacatgcaa  gctccaccgg  gtgcaaagcg  gcagcggcgg
12001  caggatatat  tcaattgtaa  atggcttcat  gtccgggaaa  tctacatgga
12051  tcagcaatga  gtatgatggt  caatatggag  aaaaagaaag  agtaattacc
12101  aatttttttt  caattcaaaa  atgtagatgt  ccgcagcgtt  attataaaat
12151  gaaagtacat  tttgataaaa  cgacaaatta  cgatccgtcg  tatttatagg
12201  cgaaagcaat  aaacaaatta  ttctaatccg  gaaatctttta  tttcgacgtg
12251  tctacattca  cgtccaaatg  ggggcggcga  att
```

FIG.11 (cont'd)

SEQUENCE LISTING

```
<160> NUMBER OF SEQ ID NOS: 7

<210> SEQ ID NO 1
<211> LENGTH: 427
<212> TYPE: PRT
<213> ORGANISM: Arabidopsis thaliana

<400> SEQUENCE: 1

Met Lys Ala Ile Gln Leu Leu Trp Glu Ala Ile Met Glu Ala Thr Lys
1               5                   10                  15

Arg Glu Arg Arg Arg Glu Asp Asp Asp Gly Glu Lys Ala Ser Pro Glu
            20                  25                  30

Ser Leu Val Leu Pro Pro Glu Ile Ile Thr Glu Ile Leu Leu Arg Leu
        35                  40                  45

Pro Ala Lys Ser Ile Gly Arg Phe Arg Cys Val Ser Lys Leu Phe Cys
    50                  55                  60

Thr Leu Ser Ser Asp Pro Gly Phe Ala Lys Ile His Leu Asp Leu Ile
65                  70                  75                  80

Leu Arg Asn Glu Ser Val Arg Ser Leu His Arg Lys Leu Ile Val Ser
                85                  90                  95

Ser His Asn Leu Tyr Ser Leu Asp Phe Asn Ser Ile Gly Asp Gly Ile
            100                 105                 110
```

```
Arg Asp Leu Ala Ala Val Glu His Asn Tyr Pro Leu Lys Asp Asp Pro
            115                 120                 125

Ser Ile Phe Ser Glu Met Ile Arg Asn Tyr Val Gly Asp His Leu Tyr
130                 135                 140

Asp Asp Arg Arg Val Met Leu Lys Leu Asn Ala Lys Ser Tyr Arg Arg
145                 150                 155                 160

Asn Trp Val Glu Ile Val Gly Ser Ser Asn Gly Leu Val Cys Ile Ser
                165                 170                 175

Pro Gly Glu Gly Ala Val Phe Leu Tyr Asn Pro Thr Thr Gly Asp Ser
            180                 185                 190

Lys Arg Leu Pro Glu Asn Phe Arg Pro Lys Ser Val Glu Tyr Glu Arg
        195                 200                 205

Asp Asn Phe Gln Thr Tyr Gly Phe Gly Phe Asp Gly Leu Thr Asp Asp
    210                 215                 220

Tyr Lys Leu Val Lys Leu Val Ala Thr Ser Glu Asp Ile Leu Asp Ala
225                 230                 235                 240

Ser Val Tyr Ser Leu Lys Ala Asp Ser Trp Arg Arg Ile Cys Asn Leu
                245                 250                 255

Asn Tyr Glu His Asn Asp Gly Ser Tyr Thr Ser Gly Val His Phe Asn
            260                 265                 270

Gly Ala Ile His Trp Val Phe Thr Glu Ser Arg His Asn Gln Arg Val
        275                 280                 285

Val Val Ala Phe Asp Ile Gln Thr Glu Glu Phe Arg Glu Met Pro Val
    290                 295                 300

Pro Asp Glu Ala Glu Asp Cys Ser His Arg Phe Ser Asn Phe Val Val
305                 310                 315                 320

Gly Ser Leu Asn Gly Arg Leu Cys Val Val Asn Ser Cys Tyr Asp Val
                325                 330                 335

His Asp Asp Ile Trp Val Met Ser Glu Tyr Gly Glu Ala Lys Ser Trp
            340                 345                 350

Ser Arg Ile Arg Ile Asn Leu Leu Tyr Arg Ser Met Lys Pro Leu Cys
        355                 360                 365

Ser Thr Lys Asn Asp Glu Glu Val Leu Leu Glu Leu Asp Gly Asp Leu
    370                 375                 380

Val Leu Tyr Asn Phe Glu Thr Asn Ala Ser Ser Asn Leu Gly Ile Cys
385                 390                 395                 400

Gly Val Lys Leu Ser Asp Gly Phe Glu Ala Asn Thr Tyr Val Glu Ser
                405                 410                 415

Leu Ile Ser Pro Asn Ser Tyr Gly Ile Glu Ser
            420                 425

<210> SEQ ID NO 2
<211> LENGTH: 1708
<212> TYPE: DNA
<213> ORGANISM: Arabidopsis thaliana

<400> SEQUENCE: 2
tttttcaaat caaatcagaa tacattgatt ctgtatatct tattgaaaaa tccatcaatt      60
tacatcaaca attttatatc taataattaa tttaaagaga aaatttataa aagtttatta     120
gagcaaataa ctcaaactcg gattttatag tcgttatgac ccggtttgac tattgaaccg     180
tttaaccgag aaattgggac tcaattaaga caaccgaaac tagacccgga tccagtgtta     240
gcgggctaga ttaaggtgtc gggtcatagc ggagaagcaa ccagacgcca acaatgaaag     300
cgatccagtt gctgtgggaa gcgataatgg aggcgacgaa gagagaaaga cggagagaag     360
```

```
atgacgacgg cgaaaaagct tcaccggaat cactcgttct tccaccagag atcattacag    420
aaattcttct ccgattacca gccaaatcga tcgggcgatt caggtgcgta tcaaagctct    480
tttgcacttt atcgtcagat ccagggttcg cgaagattca cctcgatctg atccttcgaa    540
acgaatccgt aagatcgctc caccgtaagc tcattgtgtc ttcacataat ctgtactcgt    600
tagatttcaa ttcgatcggt gacggaatta gggatttagc ggctgtggaa cacaattatc    660
ctcttaaaga cgatccaagc attttctctg agatgattag gaattacgtg ggggaccatc    720
tgtacgatga tcgtcgcgtg atgcttaagc tgaatgcgaa atcgtatcga agaaactggg    780
ttgagatcgt tggatcttcc aatggtttag tgtgtatctc tcctggtgaa ggagctgttt    840
tcttgtataa tccaactacc ggagattcca agagattacc tgaaaatttt cgtcccaaat    900
ctgtagaata cgaaagagat aatttccaaa cttatggatt tggtttcgat ggtctcactg    960
atgattacaa attggtgaag cttgttgcta ccagtgaaga tattctcgat gctagtgtct   1020
attccttgaa ggctgactca tggagacgga tctgcaattt gaattatgag cacaacgatg   1080
gctcctacac gtccggtgtg catttcaacg gtgcgattca ctgggtgttc acagagagta   1140
ggcacaacca agagtggtt gtagcatttg atattcaaac cgaggagttt cgagagatgc   1200
cagtgcctga tgaagctgaa gattgttccc ataggtttag caactttgtg gtcggaagtc   1260
tcaatggacg tctctgtgtg gtcaatagtt gctacgatgt gcatgatgat atatgggtga   1320
tgagtgagta cggtgaagct aaatcctgga gcagaattcg aatcaacttg ttgtataggt   1380
cgatgaaacc gctctgttcg actaagaacg atgaagaggt tcttctggag cttgatggag   1440
acctggtgtt gtacaacttt gaaccaatg catcgagtaa tctaggaatt tgtggggtta   1500
agctcagtga cgggttcgag gcaaatacat acgtagagag cctcatatca cccaactctt   1560
atggtataga gagctgagga agtctgcttt ttgctaagat ataataaacc aacattcgga   1620
ttagaaatgt tttagaaaca taatcatgta atatgtatca tgtaattaac aacgaatggt   1680
caatgggtat tttaagtttc tttctcct                                      1708

<210> SEQ ID NO 3
<211> LENGTH: 28
<212> TYPE: DNA
<213> ORGANISM: Artificial Sequence
<220> FEATURE:
<223> OTHER INFORMATION: Synthetic primer

<400> SEQUENCE: 3
caccaaacaa tggaggcgac gaagagag                                        28

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
atcttagcaa aaagcagact tc                                              22

<210> SEQ ID NO 5
<211> LENGTH: 1283
<212> TYPE: DNA
<213> ORGANISM: Arabidopsis thaliana

<400> SEQUENCE: 5
```

```
caccaaacaa tggaggcgac gaagagagaa agacggagag aagatgacga cggcgaaaaa        60
gcttcaccgg aatcactcgt tcttccacca gagatcatta cagaaattct tctccgatta      120
ccagccaaat cgatcgggcg attcaggtgc gtatcaaagc tcttttgcac tttatcgtcg      180
gatccagggt tcgcgaagat tcacctcgat ctgatccttc gaaacgaatc cgtaagatcg      240
ctccaccgta agctcattgt gtcttcacat aatctgtact cgttagattt caattcgatc      300
ggtgacggaa ttagggattt agcggctgtg aacacaatt atcctcttaa agacgatcca       360
agcattttct ctgagatgat taggaattac gtggggacc atctgtacga tgatcgtcgc       420
gtgatgctta agctgaatgc gaaatcgtat cgaagaaact gggttgagat cgttggatct      480
tccaatggtt tagtgtgtat ctctcctggt gaaggagctg ttttcttgta taatccaact      540
accggagatt ccaagagatt acctgaaaat tttcgtccca aatctgtaga atacgaaaga      600
gataatttcc aaacttatgg atttggtttc gatggtctca ctgatgatta caaattggtg      660
aagcttgttg ctaccagtga agatattctc gatgctagtg tctattcctt gaaggctgac      720
tcatggagac ggatctgcaa tttgaattat gagcacaacg atggctccta cacgtccggt      780
gtgcatttca acggtgcgat tcactgggtg ttcacagaga gtaggcacaa ccaaagagtg      840
gttgtagcat ttgatattca aactgaggag tttcgagaga tgccagtgcc tgatgaagct      900
gaagattgtt cccataggtt tagcaacttt gtggtcggaa gtctcaatgg acgtctctgt      960
gtggtcaata gttgctacga tgtgcatgat gatatatggg tgatgagtga gtacggtgaa     1020
gctaaatcct ggagcagaat tcgaatcaac ttgttgtata ggtcgatgaa accgctctgt     1080
tcgactaaga acgatgaaga ggttcttctg gagcttgatg gagacctggt gttgtacaac     1140
tttgaaacca atgcatcgag taatctagga atttgtgggg ttaagctcag tgacgggttc     1200
gaggcaaata catacgtaga gagcctcata tcacccaact cttatggtat agagagctga     1260
ggaagtctgc tttttgctaa gat                                              1283

<210> SEQ ID NO 6
<211> LENGTH: 12283
<212> TYPE: DNA
<213> ORGANISM: Artificial Sequence
<220> FEATURE:
<223> OTHER INFORMATION: Synthetic nucleotide construct
<220> FEATURE:
<221> NAME/KEY: misc_feature
<222> LOCATION: (10178)..(10179)
<223> OTHER INFORMATION: n is a, c, g, or t

<400> SEQUENCE: 6
ggccgcaaca gaggtggatg gacagacccg ttcttacacc ggactgggcg cgggatagga       60
tattcagatt gggatgggat tgagcttaaa gccggcgctg agaccatgct caaggtaggc      120
aatgtcctca gcgtcgagcc cggcatctat gtcgagggca ttggtggagc gcgcttcggg      180
gataccgtgc ttgtaactga gaccggatat gaggccctca ctccgcttga tcttggcaaa      240
gatatttgac gcattattta gtatgtgtta atttcattt gcagtgcagt attttctatt       300
cgatctttat gtaattcgtt acaattaata atattcaaa tcagattatt gactgtcatt      360
tgtatcaaat cgtgttaat ggatattttt attataatat tgatgatatc tcaatcaaaa     420
cgtagataat aataatattt atttaatatt tttgcgtcgc acagtgaaaa tctatatgag      480
attacaaaat accgcacaaca ttatttaaga tacatagaca ttaaccctga gactgttgga     540
cagagctcat tggtacctca gatctgggta actggcctaa ctggcttgg aggagctggc       600 aactcaaaat ccctttgcca aaaaccaaca tcatgccatc caccatgctt gtatccagct      660
```

```
gcgcgcaatg taccccgggc tgtgtatccc aaagcctcat gcaacctaac agatggatcg    720
tttggaaggc ctataacagc aaccacagac ttaaaacctt gcgcctccat agacttaagc    780
aaatgtgtgt acaatgtgga tcctaggccc aacctttgat gcctatgtga cacgtaaaca    840
gtactctcaa ctgtccaatc gtaagcgttc ctagccttcc agggcccagc gtaagcaata    900
ccagccacaa caccctcaac ctcagcaacc aaccaagggt atctatcttg caacctctct    960
agatcatcaa tccactcttg tggtgtttgt ggctctgtcc taaagttcac tgtagacgtc   1020
tcaatgtaat ggttaacgat atcacaaacc gcggccatat cagctgctgt agctggccta   1080
atctcaactg gtctcctctc cggagaagcc atggtttgga tccacaaact tacaaatttc   1140
tctgaagttg tatcctcagt acttcaaaga aaatagctta caccaatttt ttcttgtttt   1200
cacaaatgcc gaacttggtt ccttatatag gaaaactcaa gggcaaaaat gacacggaaa   1260
aatataaaag gataagtagt gggggataag attcctttgt gataaggtta ctttccgccc   1320
ttacattttc cacctacat gtgtcctcta tgtctctttc acaatcaccg accttatctt   1380
cttcttttca ttgttgtcgt cagtgcttac gtcttcaaga ttcttttctt cgcctggttc   1440
ttctttttca atttctacgt attcttcttc gtattctggc agtataggat cttgtatctg   1500
tacattcttc attttgaac ataggttgca tatgtgccgc atattgatct gcttcttgct   1560
gagctcacat aatacttcca tagttttccc cgtaaacatt ggattcttga tgctacatct   1620
tggataatta ccttctggcc ggccgcgaat tcgttggtag ggtgctagga aacttgtttt   1680
tggggttttg tataagggtt gaaacatccc tgaagtgtct catttatttt tatttattct   1740
ttgctgataa aaaaataaaa taaaagaagc taagcacacg gtcaaccatt gctctactgc   1800
taaaagggtt atgtgtagtg ttttactgca taaattatgc agcaaacaag acaactcaaa   1860
ttaaaaaatt tcctttgctt gttttttttgt tgtctctgac ttgactttct tgtggaagtt   1920
ggttgtataa ggattgggac accattgtcc ttcttaattt aattttattc tttgctgata   1980
aaaaaaaaaa atttcatata gtgttaaata ataatttgtt aaataaccaa aaagtcaaat   2040
atgtttactc tcgtttaaat aattgagatt cgttccagca aggctaaacg attgtataga   2100
tttatgacaa tatttacttt tttatagata aatgttatat tataataaat ttatatacat   2160
atattatatg ttatttatta tttattatta ttttaaatcc ttcaatattt tatcaaacca   2220
actcataatt ttttttttat ctgtaagaag caataaaatt aaatagaccc actttaagga   2280
tgatccaacc tttatacaga gtaagagagt tcaaatagta ccttttcata tacatatcaa   2340
ctaaatatt agaaatatca tggatcaaac cttataaaga cattaaataa gtggataagt   2400
ataatatata aatgggtagt atataatata taaatggata caaacttctc tctttataat   2460
tgttatgtct ccttaacatc ctaatataat acataagtgg gtaatatata atatataaat   2520
ggagacaaac ttcttccatt ataattgtta tgtcttctta acacttatgt ctcgttcaca   2580
atgctaaagt tagaattgtt tagaaagtct tatagtacac atttgttttt gtactatttg   2640
aagcattcca taagccgtca cgattcagat gatttataat aataagagga aatttatcat   2700
agaacaataa ggtgcataga tagagtgtta atatatcata acatcctttg tttattcata   2760
gaagaagtga gatggagctc agttattata ctgttacatg gtcggataca atattccatg   2820
ctctccatga gctcttacac ctacatgcat tttagttcat actggtgacc ctcgaggcga   2880
tcgctttggc cggccatttta aatggcgcgc ctttgcccgg gctttcctgc agggtttatc   2940
aaccactttg tacaagaaag ctgaacgaga aacgtaaaat gatataaata tcaatatatt   3000
```

```
aaattagatt ttgcataaaa aacagactac ataatactgt aaaacacaac atatccagtc    3060
actatggtcg acctgcagac tggctgtgta taagggagcc tgacatttat attccccaga    3120
acatcaggtt aatggcgttt ttgatgtcat tttcgcggtg gctgagatca gccacttctt    3180
ccccgataac ggagaccggc acactggcca tatcggtggt catcatgcgc cagctttcat    3240
ccccgatatg caccaccggg taaagttcac gggagacttt atctgacagc agacgtgcac    3300
tggccagggg gatcaccatc cgtcgcccgg gcgtgtcaat aatatcactc tgtacatcca    3360
caaacagacg ataacggctc tctcttttat aggtgtaaac cttaaactgc atttcaccag    3420
tccctgttct cgtcagcaaa agagccgttc atttcaataa accgggcgac ctcagccatc    3480
ccttcctgat tttccgcttt ccagcgttcg gcacgcagac gacgggcttc attctgcatg    3540
gttgtgctta ccagaccgga gatattgaca tcatatatgc cttgagcaac tgatagctgt    3600
cgctgtcaac tgtcactgta atacgctgct tcatagcaca cctcttttg acatacttcg    3660 ggtatacata tcagtatata ttcttatacc gcaaaaatca gcgcgcaaat acgcatactg    3720
ttatctggct tttagtaagc cggatccaga tctttacgcc ccgccctgcc actcatcgca    3780
gtactgttgt aattcattaa gcattctgcc gacatggaag ccatcacaga cggcatgatg    3840
aacctgaatc gccagcggca tcagcacctt gtcgccttgc gtataatatt tgcccatggt    3900
gaaaacgggg gcgaagaagt tgtccatatt ggccacgttt aaatcaaaac tggtgaaact    3960
cacccaggga ttggctgaga cgaaaaacat attctcaata aacccttag ggaaataggc    4020 caggttttca ccgtaacacg ccacatcttg cgaatatatg tgtagaaact gccggaaatc    4080
gtcgtggtat tcactccaga gcgatgaaaa cgtttcagtt tgctcatgga aaacggtgta    4140
acaagggtga acactatccc atatcaccag ctcaccgtct ttcattgcca tacggaattc    4200
cggatgagca ttcatcaggc gggcaagaat gtgaataaag gccggataaa acttgtgctt    4260
atttttcttt acggtcttta aaaaggccgt aatatccagc tgaacggtct ggttataggt    4320
acattgagca actgactgaa atgcctcaaa atgttcttta cgatgccatt gggatatatc    4380
aacggtggta tatccagtga tttttttctc catttagct tccttagctc ctgaaaatct    4440
cgccggatcc taactcaaaa tccacacatt atacgagccg gaagcataaa gtgtaaagcc    4500
tggggtgcct aatgcggccg ccatagtgac tggatatgtt gtgttttaca gtattatgta    4560
gtctgttttt tatgcaaaat ctaatttaat atattgatat ttatatcatt ttacgtttct    4620
cgttcagctt ttttgtacaa acttgttgat aaacttaatt aaggatccta gagtagtatt    4680
gaatatgagt tgggttgggg tattatagta gtagagtagt agtactctgg atggatggat    4740
gatgaaagaa gtgagtgata ttagaggtat ttataggtat tatataagag agaaggtggt    4800
tggaacatgc atggagattt gggcatggga tgacacgcat atgcaggttg acgtgtgttg    4860
aagtgaagaa attgaggtgg cggaagagaa tgaatatata caggtggttg tggtgatgat    4920
gaagaaaaag gcaatgtgtt tgtgtgtggg ttgagatggg tgagccattt aaagtgcatg    4980
ttaagcacgt gttgctttgc atggcattta gacatacatg gacgcggcga tcttgatcag    5040
ccagtgacta atttgagttg gttgtgtgat tgcgttttgt ctctctgttt tgtcttttt     5100 ctttgttctt tgtctttttc ttgcgcaagc atccatgcat gaaccaaaag accacagagt    5160
gtcatggcaa cccacagtaa ttccagttac ggacttacat accaagaaaa ggtaaaagca    5220
ataagaaata tatgaaaatt agtccaccat aaatcttata gtttatggtt tagggtaaca    5280
ctctaacact ctactacatt acttatattt actttaaact atctataaaa caatttaaac    5340
atagtagaat aataaatcaa tagtcacaaa ttcaacaatt aaacttaaaa ttaaaaaagt    5400
```

```
aatatttta   ttatatctaa   ttaattttt   agaagtaata   ttgagtattt   gatatatgaa      5460
atcttgaata   tagtaactat   tattaaaatt   actttagaag   atgtgtctcg   catgtaaaag      5520
cagatcttca   gttacttccg   tagtgtcaaa   tgggaattat   agaattttgc   ataacatgac      5580
ttgcttcaga   aataccacaa   atcattgttt   ggtgaaattt   tcattgtata   aaaaaaatac      5640
aatgataatt   ggattttttt   attcaaagaa   aaaatggct    agttgtgtca   ctgggtgttg      5700
ctttaagatc   agtcgaataa   aaaaattatg   gagttaaatt   ttattacttt   tgaaacaact      5760
tattattatg   agatttacgt   ggttgaaaaa   tatttgataa   atatatttt    aaaatataaa      5820 atgggaaatc   cttcttaagg   taaagaattt   gtttatattg   tatattaaac   atttatatga      5880
agaagaataa   gaataaatca   ttatgctttc   taccaacgct   aaaattaagt   aaattatata      5940
tttcaatatg   aaaatgttag   actacattaa   agatagacgg   gacttcataa   aattttatgc      6000
ggtttgaaaa   tgtttaacaa   ataataaatt   tgtagggata   tcgtgtgcgg   aagcgtgata      6060
atttcaacca   aagattatga   gaattaaag    taacaagtaa   agtgagaatg   ataccagaat      6120
ttttaggtgg   aaaacccctt   taaatagagg   taaaaaacca   ccggcgagag   agccaaaact      6180
ttcactataa   tgatactggg   agtacaatgg   cggccgggc    tgcaattgat   ccggtgagta      6240
atattgtacg   gctaagagcg   aatttggcct   gtagacctca   attgcgagct   ttctaatttc      6300
aaactattcg   ggcctaactt   tggtgtgat    gatgctgact   ggcaggatat   ataccgttgt      6360
aatttgagct   cgtgtgaata   agtcgctgtg   tatgtttgtt   tgattgtttc   tgttggagtg      6420
cagcccattt   caccggacaa   gtcggctaga   ttgatttagc   cctgatgaac   tgccgagggg      6480
aagccatctt   gagcgcggaa   tgggaatgga   tcgaaccggg   agcacaggat   gacgcctaac      6540
aattcattca   agccgacacc   gcttcgcggc   gcggcttaat   tcaggagtta   acatcatga       6600 gggaagcggt   gatcgccgaa   gtatcgactc   aactatcaga   ggtagttggc   gtcatcgagc      6660
gccatctcga   accgacgttg   ctggccgtac   atttgtacgg   ctccgcagtg   gatggcggcc      6720
tgaagccaca   cagtgatatt   gatttgctgg   ttacggtgac   cgtaaggctt   gatgaaacaa      6780
cgcggcgagc   tttgatcaac   gacctttgg    aaacttcggc   ttccctgga    gagagcgaga      6840 ttctccgcgc   tgtagaagtc   accattgttg   tgcacgacga   catcattccg   tggcgttatc      6900
cagctaagcg   cgaactgcaa   tttggagaat   ggcagcgcaa   tgacattctt   gcaggtatct      6960
tcgagccagc   cacgatcgac   attgatctgg   ctatcttgct   gacaaaagca   agagaacata      7020
gcgttgcctt   ggtaggtcca   gcggcggagg   aactctttga   tccggttcct   gaacaggatc      7080
tatttgaggc   gctaaatgaa   accttaacgc   tatggaactc   gccgcccgac   tgggctggcg      7140
atgagcgaaa   tgtagtgctt   acgttgtccc   gcatttggta   cagcgcagta   accggcaaaa      7200
tcgcgccgaa   ggatgtcgct   gccgactggg   caatggagcg   cctgccggcc   cagtatcagc      7260
ccgtcatact   tgaagctagg   caggcttatc   ttggacaaga   agatcgcttg   gcctcgcgcg      7320
cagatcagtt   ggaagaattt   gttcactacg   tgaaaggcga   gatcaccaag   gtagtcggca      7380
aataatgtct   aacaattcgt   tcaagccgac   gccgcttcgc   ggcgcggctt   aactcaagcg      7440
ttagagagct   ggggaagact   atgcgcgatc   tgttgaaggt   ggttctaagc   ctcgtacttg      7500
cgatggcatt   tcgatcgaaa   ggggtacaaa   ttcccactaa   gcgctcgggg   gctgagaaag      7560
cccagtaagg   aaacaactgt   aggttcgagt   cgcgagatcc   cccggaacca   aaggaagtag      7620
gttaaacccg   ctccgatcag   gccgagccac   gccaggccga   gaacattggt   tcctgtaggc      7680
atcgggattg   gcggatcaaa   cactaaagct   actggaacga   gcagaagtcc   tccggccgcc      7740
```

```
agttgccagg ccgtaaaggt gagcagaggc acgggaggtt gccacttgcg ggtcagcacg    7800
gttccgaacg ccatggaaac cgccccgcc aggcccgctg cgacgccgac aggatctagc    7860
gctgcgtttg gtgtcaacac caacagcgcc acgcccgcag ttccgcaaat agccccagg    7920 accgccatca atcgtatcgg gctacctagc agagcggcag agatgaacac gaccatcagc    7980
ggctgcacag cgcctaccgt cgccgcgacc cgcccggcag gcggtagacc gaaataaaca    8040
acaagctcca gaatagcgaa atattaagtg cgccgaggat gaagatgcgc atccaccaga    8100
ttcccgttgg aatctgtcgg acgatcatca cgagcaataa acccgccggc aacgcccgca    8160
gcagcatacc ggcgacccct cggcctcgct gttcgggctc cacgaaaacg ccggacagat    8220
gcgccttgtg agcgtccttg gggccgtcct cctgtttgaa gaccgacagc ccaatgatct    8280
cgccgtcgat gtaggcgccg aatgccacgg catctcgcaa ccgttcagcg aacgcctcca    8340
tgggcttttt ctcctcgtgc tcgtaaacgg acccgaacat ctctggagct ttcttcaggg    8400
ccgacaatcg gatctcgcgg aaatcctgca cgtcggccgc tccaagccgt cgaatctgag    8460
ccttaatcac aattgtcaat tttaatcctc tgtttatcgg cagttcgtag agcgcgccgt    8520
gcgcccgagc gatactgagc gaagcaagtg cgtcgagcag tgcccgcttg ttcctgaaat    8580
gccagtaaag cgctggctgc tgaaccccca gccggaactg accccacaag gcctagcgt     8640 ttgcaatgca ccaggtcatc attgacccag gcgtgttcca ccaggccgct gcctcgcaac    8700
tcttcgcagg cttcgccgac ctgctcgcgc cacttcttca cgcgggtgga atccgatccg    8760
cacatgaggc ggaaggtttc cagcttgagc gggtacggct cccggtgcga gctgaaatag    8820
tcgaacatcc gtcgggccgt cggcgacagc ttgcggtact tctcccatat gaatttcgtg    8880
tagtggtcgc cagcaaacag cacgacgatt tcctcgtcga tcaggacctg caacgggac     8940 gttttcttgc cacggtccag gacgcggaag cggtgcagca gcgacaccga ttccaggtgc    9000
ccaacgcggt cggacgtgaa gcccatcgcc gtcgcctgta ggcgcgacag gcattcctcg    9060
gccttcgtgt aataccggcc attgatcgac cagcccaggt cctggcaaag ctcgtagaac    9120
gtgaaggtga tcggctcgcc gatagggtg cgcttcgcgt actccaacac ctgctgccac     9180
accagttcgt catcgtcggc ccgcagctcg acgccggtgt aggtgatctt cacgtccttg    9240
ttgacgtgga aaatgacctt gttttgcagc gcctcgcgcg ggattttctt gttgcgcgtg    9300
gtgaacaggg cagagcgggc cgtgtcgttt ggcatcgctc gcatcgtgtc cggccacggc    9360
gcaatatcga acaaggaaag ctgcatttcc ttgatctgct gcttcgtgtg tttcagcaac    9420
gcggcctgct tggcctcgct gacctgtttt gccaggtcct cgccggcggt ttttcgcttc    9480
ttggtcgtca tagttcctcg cgtgtcgatg gtcatcgact tcgccaaacc tgccgcctcc    9540
tgttcgagac gacgcgaacg ctccacggcg gccgatggcg cgggcagggc aggggagcc     9600 agttgcacgc tgtcgcgctc gatcttggcc gtagcttgct ggaccatcga gccgacggac    9660
tggaaggttt cgcggggcgc acgcatgacg gtgcggcttg cgatggtttc ggcatcctcg    9720
gcggaaaacc ccgcgtcgat cagttcttgc ctgtatgcct tccggtcaaa cgtccgattc    9780
attcaccctc cttgcgggat tgccccgact cacgccgggg caatgtgccc ttattcctga    9840 tttgaccccgc ctggtgcctt ggtgtccaga taatccacct tatcggcaat gaagtcggtc    9900
ccgtagaccg tctggccgtc cttctcgtac ttggtattcc gaatcttgcc ctgcacgaat    9960
accagcgacc ccttgcccaa atacttgccg tgggcctcgg cctgagagcc aaaacacttg   10020
atgcggaaga agtcggtgcg ctcctgcttg tcgccggcat cgttcgccca ctcttcatta   10080
accgctatat cgaaaattgc ttgcggcttg ttagaattgc catgacgtac ctcggtgtca   10140
```

```
cgggtaagat taccgataaa ctggaactga ttatggcnnc tcgaaattcc ctcggtcttg    10200
ccttgctcgt cggtgatgta cttcaccagc tccgcgaagt cgctcttctt gatggagcgc    10260
atggggacgt gcttggcaat cacgcgcacc ccccggccgt tttagcggct aaaaaagtca    10320
tggctctgcc ctcgggcgga ccacgccat catgaccttg ccaagctcgt cctgcttctc     10380
ttcgatcttc gccagcaggg cgaggatcgt ggcatcaccg aaccgcgccg tgcgcgggtc    10440
gtcggtgagc cagagtttca gcaggccgcc caggcggccc aggtcgccat tgatgcgggc    10500
cagctcgcgg acgtgctcat agtccacgac gcccgtgatt ttgtagccct ggccgacggc    10560
cagcaggtag gccgacaggc tcatgccggc cgccgccgcc ttttcctcaa tcgctcttcg    10620
ttcgtctgga aggcagtaca ccttgatagg tgggctgccc ttcctggttg gcttggtttc    10680
atcagccatc cgcttgccct catctgttac gccggcggta gccggccagc ctcgcagagc    10740
aggattcccg ttgagcaccg ccaggtgcga ataagggaca gtgaagaagg aacacccgct    10800
cgcgggtggg cctacttcac ctatcctgcc cggctgacgc cgttggatac accaaggaaa    10860
gtctacacga acctttggc aaaatcctgt atatcgtgcg aaaaaggatg gatataccga     10920
aaaaatcgct ataatgaccc cgaagcaggg ttatgcagcg gaaagatcc gtcgacccctt    10980 tccgacgctc accgggctgg ttgccctcgc cgctgggctg gcggccgtct atggccctgc    11040
aaacgcgcca gaaacgccgt cgaagccgtg tgcgagacac cgcggccgcc ggcgttgtgg    11100
ataccacgcg gaaaacttgg ccctcactga cagatgaggg gcggacgttg acacttgagg    11160
ggccgactca cccggcgcgg cgttgacaga tgaggggcag gctcgatttc ggccggcgac    11220
gtggagctgg ccagcctcgc aaatcggcga aaacgcctga ttttacgcga gtttcccaca    11280
gatgatgtgg acaagcctgg ggataagtgc cctgcggtat tgacacttga ggggcgcgac    11340
tactgacaga tgaggggcgc gatccttgac acttgagggg cagagtgatg acagatgagg    11400
ggcgcaccta ttgacatttg aggggctgtc cacaggcaga aaatccagca tttgcaaggg    11460
tttccgcccg ttttcggcc accgctaacc tgtcttttaa cctgctttta aaccaatatt    11520
tataaaccct gttttttaacc agggctgcgc cctggcgcgt gaccgcgcac gccgaagggg   11580
ggtgcccccc cttctcgaac cctccgcc cgctaacgcg ggcctcccat ccccccaggg     11640
gctgcgcccc tcggccgcga acggcctcac cccaaaaatg gcaggccaag cttgcttggt    11700
cgttccggta cgtaccgtga acgtcggctc gattgtacct gcgttcaaat actttgcgat    11760
cgtgttgcgc gcctgcccgg tgcgtcggct gatctcacgg atcgactgct tctctcgcaa    11820
cgccatccga cggatgatgt ttaaaagtcc catgtggatc actccgttgc cccgtcgctc    11880
accgtgttgg ggggaaggtg cacatggctc agttctcaat ggaaattatc tgcctaaccg    11940
gctcagttct gcgtagaaac caacatgcaa gctccaccgg gtgcaaagcg gcagcggcgg    12000
caggatatat tcaattgtaa atggcttcat gtccgggaaa tctacatgga tcagcaatga    12060
gtatgatggt caatatggag aaaaagaaag agtaattacc aatttttttt caattcaaaa    12120
atgtagatgt ccgcagcgtt attataaaat gaaagtacat tttgataaaa cgacaaatta    12180
cgatccgtcg tatttatagg cgaaagcaat aaacaaatta ttctaattcg gaaatcttta    12240
tttcgacgtg tctacattca cgtccaaatg ggggcggcga att                      12283

<210> SEQ ID NO 7
<211> LENGTH: 92
<212> TYPE: DNA
<213> ORGANISM: Artificial Sequence
<220> FEATURE:
```

```
<223> OTHER INFORMATION: Synthetic oligonucleotide

<400> SEQUENCE: 7
ggatccttaa ttaagtttaa accctgcagg aaagcccggg caaaggcgcg ccatttaaat      60
ggccggccaa agcgatcgcc tcgagggtca cc                                   92
```

F-BOX PROTEIN TARGETED PLANT OIL PRODUCTION

CROSS REFERENCE TO RELATED APPLICATIONS

This Application is a Continuation Application and claims the benefit of priority to U.S. patent application Ser. No. 12/609,562, filed Oct. 30, 2009, which is a Divisional Application and claims the benefit of priority to U.S. patent application Ser. No. 11/525,579, filed Sep. 22, 2006, which claims the benefit of priority to U.S. Provisional Application No. 60/720,424, filed Sep. 26, 2005, the contents of which are hereby incorporated by reference in their entirety and the benefit of priority is claimed herein.

FIELD OF THE INVENTION

This invention relates to the field of agriculture and plant engineering. In particular, this invention relates to methods and compositions for increasing oil content in transgenic plants, including the oil content of *Arabidopsis thaliana* seeds.

BACKGROUND OF THE INVENTION

Plant oils represent a renewable resource of highly reduced carbon. Current world vegetable oil production is estimated at 87 million metric tons with an approximate market value of some 40 billion U.S. dollars. The majority of vegetable oil currently goes directly to human consumption and as much as 25% of human caloric intake in developed countries is derived from plant fatty acids (Broun et al. (1999) *Ann. Rev. Nutr.* 19: 197-216). In addition to their importance in human nutrition, plant fatty acids are also major ingredients of non-food products such as soaps, detergents, lubricants, biofuels, cosmetics, and paints (see Ohlrogge (1994) *Plant Physiol.* 104: 821-6). While the demand for vegetable oils has increased steadily, production capacity to meet this demand is more than adequate and prices of vegetable oils have remained below or near 0.6 U.S. dollars per kilogram. This low cost of production has stimulated interest in use of vegetable oils as renewable alternatives to petroleum-derived chemical feedstocks.

Fatty acids are the most abundant form of reduced carbon chains available from nature and have diverse uses ranging from food to industrial feedstocks. Plants represent a significant renewable source of fatty acids because many species accumulate them in the form of triacylglycerol as major storage components in seeds. With the advent of plant transformation technology, metabolic engineering of oilseed fatty acids has become possible and transgenic plant oils represent some of the first successes in design of modified plant products. For example, the transfer of a California bay plant thioesterase gene into the seeds on non-laurate (12:0)-accumulating plants, *Arabidopsis* and *Brassica napus* (rapeseed) resulted in the alteration of the fatty acid acyl chain elongation process to produce laurate up to 24% and 58% of total seed fatty acids, respectively (see Voelker et al. (1992) *Sci.* 257: 72-4; and Voelker et al. (1996) *Plant J.* 9: 229-41 respectively). Thus, the transfer of a single gene into a plant can dramatically alter the type of fatty acids produced.

However, such success with a single gene is the exception rather than the rule (for review, see Thelan and Ohlrogge (2002) *Metabol. Engineer.* 4:12-21). Moreover, to be economically useful for both human consumption and industrial uses, an actual increase in seed oil fatty acid content, rather than just a change in the type of fatty acid produced, would be highly desirable. While the production of malonlyl-CoA by acetyl-CoA carboxylase is a key regulatory step in the de novo synthesis of fatty acids, attempts to increase the rate of this apparently rate-limiting step by genetic engineering have met with, at best, modest success. Furthermore, the overexpression of several individual fatty acid synthase enzymes has not resulted in an increased flux of fatty acid biosynthesis (reviewed in Thelan and Ohlrogge (2002) *Metabol. Engineer.* 4:12-21).

Accordingly, there remains a need for genetic engineering strategies that will increase the total amount of fatty acid produced by plants.

SUMMARY OF THE INVENTION

The invention is based, in part, upon the unexpected finding that overexpression of F-box genes in plants results in the increased production of plant oil. In particular, the overexpression of the *Arabidopsis thaliana* F-box protein (GenBank Accession Nos. NM_111499 (cDNA) and NP_566277 (protein) using the seed specific promoter phaseolin, produced seeds with a higher oil content phenotype (see FIGS. 1-5).

Accordingly, in one aspect, the invention provides a genetic construct for the overexpression of an F-box protein in plants. In general, such genetic constructs of the invention include a gene promoter sequence; and a sequence encoding a plant F-box protein that is functionally linked to the gene promoter sequence. In some embodiments, the F-box protein is a plant F-box protein or encoded by a plant F-box gene. In other embodiments, the F-box protein is a non-plant F-box protein or encoded by a non-plant F-box gene, such as an animal (e.g., a mammal) F-box protein or gene. In some embodiments, the gene promoter sequence is a seed-specific promoter. In particularly useful embodiments, the gene promoter sequence is phaseolin. In certain particularly useful embodiments, the genetic construct comprises a pBBV-PHAS expression vector.

In further embodiment, the genetic constructs of the invention comprise a sequence that encodes the plant F-box protein has a polypeptide sequence that is at least 75% identical to the polypeptide sequence of SEQ ID NO: 1. In other embodiments, the plant F-box protein has a polypeptide sequence that is at least 90% identical to the polypeptide sequence of SEQ ID NO: 1. In still further useful embodiments, the genetic constructs of the invention comprise an plant F-box protein having the polypeptide sequence of SEQ ID NO: 1. In particular embodiments, the plant F-box protein is encoded by the nucleic acid sequence of SEQ ID NO: 2. In further embodiments, the F-box protein is encoded by a nucleic acid that hybridizes to the nucleic acid sequence of SEQ ID NO: 2. In particularly useful embodiments, the F-box protein is encoded by a nucleic acid that hybridizes under stringent conditions to the nucleic acid sequence of SEQ ID NO: 2.

In another aspect, the invention provides transgenic plant cells comprising any of the above-described genetic constructs of the invention. In certain useful embodiments, the transgenic plant cell is an *Arabidopsis thaliana*. In other embodiments, the transgenic plant cell is an agricultural crop plant, such as corn or wheat. In other embodiments, the transgenic plant cell is an oil-producing agricultural crop such as soybean, palm, rapeseed or sunflower.

In a further aspect, the invention provides a recombinant *Arabidopsis thaliana* plant cell having an heterologous genetic construct that includes a gene promoter sequence functionally linked to a plant F-box encoding sequence. In certain particularly useful embodiments, the F-box sequence encoded corresponds to the plant F-box polypeptide of SEQ ID NO: 1 and the promoter is phaseolin.

In yet another aspect, the invention provides a plant having a transgenic plant cell of the invention, as described above, or a part, propagule or progeny thereof comprising one of the genetic constructs of the invention.

In still another aspect, the invention provides a method of modifying oil production in a plant by, first, stably incorporating into the genome of the plant a genetic construct of the invention, as described above, to provide a transformed plant, and, then, regenerating the transformed plant so that expression of the incorporated genetic construct modifies oil production in the plant. In particular embodiments, the plant modified is *Arabidopsis thaliana*. In other embodiments, the plant is an agricultural crop plant, such as corn or wheat. In further embodiments, the plant is an oil-producing agricultural crop such as soybean, palm, rapeseed or sunflower.

BRIEF DESCRIPTION OF THE DRAWINGS

FIG. 10A is the polypeptide sequence of an *Arabidopsis thaliana* F-box protein corresponding to GenBank Accession No. NP_566277 (SEQ ID NO: 1).

FIG. 10B is the nucleotide sequence of an *Arabidopsis thaliana* F-box protein corresponding to GenBank Accession No. NM_111499 (SEQ ID NO: 2). The predicted initiation and termination codons of the F-box protein open reading frame are underlined.

FIG. 11 and the FIG. 11 (cont'd) pages show the nucleic acid sequence (SEQ ID NO: 6) of pGATE-PHASE: F-box, with the inserted F-box encoding sequences shown in capital letters.

DETAILED DESCRIPTION OF THE INVENTION

Figure 1:
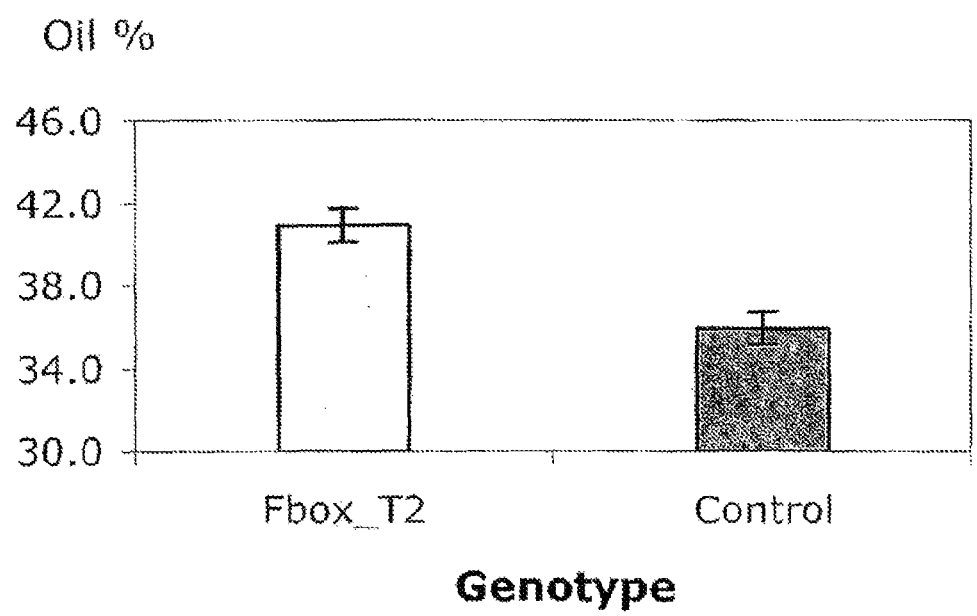
FIG. 1 is a graphical representation of experiments demonstrating the increased oil content of transgenic phaseolin-F-box lines compared with vector control lines. Data shown are average of 18 lines (T2) and error bars are SE.

The patent and scientific literature referred to herein establishes knowledge that is available to those of skill in the art. The issued. U.S. patents, allowed applications, published foreign applications, and references, including GenBank database sequences, that are cited herein are hereby incorporated by reference to the same extent as if each was specifically and individually indicated to be incorporated by reference.

General

The invention is based in part upon the unexpected discovery that overexpression of plant F-box proteins increases the oil content of plant seeds. In particular, the overexpression of the *Arabidopsis thaliana* F-box protein (GenBank Accession Nos. NM_111499 (cDNA) and NP_566277 (protein)) using the seed specific promoter phaseolin, produced seeds with a higher fatty acid content phenotype (see FIGS. 1-5). Accordingly, in general, the invention provides transgenic plants incorporating heterologous F-box genes that increase the oil content of one or more developmental stages of a vascular plant.

Fatty acids stored in plant seeds are usually unbranched compounds with an even number of carbons ranging from 12 to 22 and with 0 to 3 cis double bonds. However, numerous variations on this theme exist in nature particularly with regard to additional functional groups such as hydroxyl, epoxy, cyclopropene, or acetylenic. Plants represent a large reservoir of fatty acid diversity, synthesizing at least 200 different types of fatty acids (see van de Loo et al., (1993) "Unusual fatty acids" in *Plant Lipids* (T. Moore, Ed.), pp. 91-126, CRC, Boca Raton, Fla.). Human use, however, has been predominantly restricted to a select few fatty acids that accumulate in domesticated plants. The four most important oilseed crops are, in descending order, soybean, oil palm, rapeseed, and sunflower, which together account for 65% of current worldwide vegetable oil production. The abundant fatty acids produced in these major commercial oilseeds comprise just four of the more than 200 possibilities, namely linoleate, palmitate, laurate, and oleate.

With regard to lipid nomenclature, a simple shorthand notation based on molecule length and the number and position of double bonds has been developed to designate fatty acids. For example, the common monounsaturated fatty acid oleic acid (octadecenoic acid) is designated 18:1. The first value, 18, represents the number of carbons. The second value, 1, indicates the number of double bonds. In addition, the position of the double bonds, counting from the carboxyl group is designated by delta ($\Delta$) and oleic acid can be more fully designated as 18:1 $\Delta$9. The double bonds in naturally occurring fatty acids are almost exclusively cis isomers, and usually no designation for the type of double bond is used unless it is a trans isomer, as in 16:1 $\Delta$3t. Some authors also designate the positions of the double bonds relative to the terminal methyl carbon. Thus, an omega-3 fatty acid contains a double bond 3 carbons from the methyl end of the fatty acid (e.g., 18:3 Δ9, 12, 15 is an omega-3 fatty acid). The position at which a fatty acid is esterified to the glycerol backbone of glycerolipids is designated sn-3 (the terminal hydroxyl that is phosphorylated in glycerol 3-phosphate), sn-2 (the central hydroxyl), and sn-1 (the terminal hydroxyl that is not phosphorylated).

For both edible and industrial uses, an increase in seed oil content is desirable and has been a major goal of oilseed engineering. However, to be economically useful, such a change must not come at the expense of overall seed yield or at the loss of other high-value components. For example, soybean is the largest source of vegetable oil, comprising 30% of the world market, and now constitutes over 80% of all dietary vegetable oils in the United States. Although termed an oilseed, soybean contains only 18-22% oil on a seed dry-weight basis and is grown principally as a high-protein meal for animal feeds. Thus, increasing oil in soybean will in most cases not be useful if it comes at the expense of high-value soy protein that drives the crop's economics. By comparison, other oilseed crops (except cotton) are grown primarily for their oil and produce seeds with 40-60% oil. The wide range of seed oil percentage observed in nature suggests that this pathway might be amenable to metabolic engineering, particularly in "low-oil" oilseeds, provided the key mechanisms which control oil content are identified.

Definitions

For convenience, the meaning of certain terms and phrases employed in the specification, examples, and appended claims are provided below.

The term "agonist", as used herein, is meant to refer to an agent that mimics or upregulates (e.g. potentiates or supplements) a bioactivity. For example, an F-box agonist can be a wild-type F-box protein or derivative thereof having at least one bioactivity of the wild-type F-box protein. An agonist can also be a compound which increases the interaction of a bioactive polypeptide with another molecule, for example, a receptor. Agonists can be any class of molecule, such as a small molecule, including a nucleic acid, protein, carbohydrate, lipid or combination thereof.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. Alleles of a specific gene can differ from each other in a single nucleotide, or several nucleotides, and can include substitutions, deletions, and insertions of nucleotides. Frequently occurring sequence variations include transition mutations (i.e. purine to purine substitutions and pyrimidine to pyrimidine substitutions, e.g. A to G or C to T), transversion mutations (i.e. purine to pyrimidine and pyrimidine to purine substitutions, e.g. A to T or C to G), and alteration in repetitive DNA sequences (e.g. expansions and contractions of trinucleotide repeat and other tandem repeat sequences). An allele of a gene can also be a form of a gene containing a mutation. The term "allelic variant of a polymorphic region of a gene" refers to a region of a locus gene having one or several nucleotide sequence differences found in that region of the gene in other individuals.

As used herein, the term "F-box" or "F-box protein" refers to the amino acid sequences of proteins involved in proteolysis, including but not limited to proteins involved in the ubiquitin-ligase complex obtained from any species, including plant species, from any source whether natural, synthetic, semi-synthetic, or recombinant. The F-box is a sequence of 35-45 amino acids and allows the F-box proteins to enter into complexes with other ubiquitin-dependent protein degradation components (e.g., Skp1). Thus, the F-box proteins may bind Skp1, and may contain a motif that displays a sequence similarity to Grr1 or Cdc4 or to the *Arabidopsis thaliana* F-box protein shown in FIG. 10A. This conserved structural motif is included in the sequence alignments shown in FIG. 7 of U.S. Pat. No. 6,573,094, the contents of which have been incorporated herein in their entirety (i.e., the amino acid residues that are shared by the F-box proteins shown). However, it is not intended that the term be limited to the exact sequences set forth herein. In some embodiments, the F-box proteins may further comprise additional motifs, in particular motifs involved in protein-protein interaction. These additional motifs included, but are not limited to leucine-rich repeats, and WD-40. In certain embodiments, the F-box protein is from a vascular plant, while in particularly useful embodiments, the F-box protein is from *Arabidopsis thaliana*.

The term "antagonist" as used herein is meant to refer to an agent that downregulates (e.g. suppresses or inhibit;) at least bioactivity. An antagonist can be a compound that inhibits or decreases the interaction between one protein and another molecule, e.g., a substrate. Accordingly, a useful antagonist is a compound that inhibits or decreases binding to a substrate and thereby blocks enzyme function. An antagonist can also be a compound that downregulates expression of a gene or genes or which reduces the amount of a gene product translated. The target bioactivity antagonist can be a dominant negative form of a polypeptide possessing that bioactivity, for example F-box antagonists would include a form of an F-box polypeptide which is capable of interacting with other components of the ubiquitin-dependent pathway, but which interferes with the function of the resulting complex (i.e. a dominant negative form of the target bioactivity). An antagonist can also be an antisense nucleic acid, or a ribozyme capable of interacting specifically with a target bioactivity-encoding mRNA. Yet other antagonists are molecules that bind to a target bioactivity and inhibit its action. Such molecules include peptides such as those which will bind the active site of an enzyme and prevent it from interacting with substrate. Yet other target bioactivity antagonists include antibodies which interact specifically with an epitope of the target polypeptide, such that binding interferes with the biological function of the polypeptide. In yet another useful embodiment, the antagonist is a small molecule, such as a molecule capable of inhibiting the interaction between a target enzyme and its substrate.

"Asexual propagation" refers to producing progeny by regenerating an entire plant from leaf cuttings, stem cuttings, root cuttings, single plant cells (protoplasts) and callus.

The term "catalytic site" refers to the portion of a molecule that is capable of binding a reactant and improving the rate of a reaction. Catalytic sites may be present on polypeptides or proteins, enzymes, organics, organo-metal compounds, metals and the like. A catalytic site may be made up of separate portions present on one or more polypeptide chains or compounds. These separate catalytic portions associate together to form a larger portion of a catalytic site. A catalytic site may be formed by a polypeptide or protein that is bonded to a metal.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject polypeptides with a second amino acid sequence defining a domain (e.g. polypeptide portion) foreign to and not substantially homologous with any domain of the subject polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-polypeptide-Y, wherein polypeptide represents a first or subject protein or polypeptide, and X and Y are independently absent or represent amino acid sequences which are not related to the first sequence in an organism, including naturally occurring mutants.

As used herein, "conservatively modified variations" of a particular nucleic acid sequence refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, COG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

As described herein, sequences may be optimized for expression in a particular host cell used to produce the protein (e.g, a plant cell such as a tomato, or a cloning and expression system such as a yeast cell). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. tobacco mosaic virus) or target cell specific binding agents (e.g. ligands recognized by target cell specific receptors). Useful complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a target polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "enzymatic site" refers to the portion of a protein molecule that contains a catalytic site. Most enzymatic sites exhibit a very high selective substrate specificity. An enzymatic site may be comprised of two or more enzymatic site portions present on different segments of the same polypeptide chain. These enzymatic site portions are associated together to form a greater portion of an enzymatic site. A portion of an enzymatic site may also be a metal.

The term "enzyme" refers to a protein, polypeptide, peptide RNA molecule, or multimeric protein capable of accelerating or producing by catalytic action some change in a substrate for which it is often specific.

The term "epitope" refers to portion of a molecule that is specifically recognized by an immunoglobulin product. It is also referred to as the determinant or antigenic determinant.

As used herein, an "immunoglobulin" is a multimeric protein containing the immunologically active portions of an immunoglobulin heavy chain and immunoglobulin light chain covalently coupled together and capable of specifically combining with antigen.

As used herein, a Fab fragment is a multimeric protein consisting of the portion of an immunoglobulin molecule containing the immunologically active portions of an immunoglobulin heavy chain and an immunoglobulin light chain covalently coupled together and capable of specifically combining with antigen. Fab fragments are typically prepared by proteolytic digestion of substantially intact immunoglobulin molecules with papain using methods that are well known in the art. However, a Fab fragment may also be prepared by expressing in a suitable host cell the desired portions of immunoglobulin heavy chain and immunoglobulin light chain using methods well known in the art.

As used herein, an F[v]fragment: A multimeric protein consisting of the immunologically active portions of an immunoglobulin heavy chain variable region and an immunoglobulin light chain variable region covalently coupled together and capable of specifically combining with antigen. F[v]fragments are typically prepared by expressing in suitable host cell the desired portions of immunoglobulin heavy chain variable region and immunoglobulin light chain variable region using methods well known in the art.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides, which may optionally include intron sequences which are either derived from a chromosomal DNA. Exemplary recombinant genes include those which encode an F-box polypeptide activity.

As used herein, "heterologous DNA" or "heterologous nucleic acid" include DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA, Any DNA that one of skill in the art would recognize or consider as heterologous or foreign to the cell in which is expressed is herein encompassed by heterologous DNA. Examples of heterologous DNA include, but are not limited to, isolated DNA that encodes an F-box protein.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, or less than 25% identity, with one of the sequences of the present invention.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive (constitutively or inducibly). Inactivation may be partial or total.

The term "interact" as used herein is meant to include detectable relationships or association (e.g. biochemical interactions) between molecules, such as interaction between protein-protein, protein-nucleic acid, nucleic acid-nucleic acid, and protein-small molecule or nucleic acid-small molecule in nature.

The term "isolated" as also used herein with respect to nucleic acids, such as DNA or RNA, refers to molecules separated from other DNAs, or RNAs, respectively, that are present in the natural source of the macromolecule. For example, isolated nucleic acids encoding the subject polypeptides typically include no more than 10 kilobases (kb) of nucleic acid sequence which naturally immediately flanks that gene in genomic DNA, or no more than 5 kb of such naturally occurring flanking sequences, and most usefully less than 1.5 kb of such naturally occurring flanking sequence. The term isolated as used herein also refers to a nucleic acid or polypeptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "knock-out" refers to partial or complete suppression of the expression of an endogenous gene. This is generally accomplished by deleting a portion of the gene or by replacing a portion with a second sequence, but may also be caused by other modifications to the gene such as the introduction of stop codons, the mutation of critical amino acids, the removal of an intron junction, etc.

The term "marker" or "marker sequence" or similar phrase means any gene that produces a selectable genotype or a selectable phenotype. It includes such examples as the spectinomycin gene (spcR), neo gene (neoR), green fluorescent protein (GFP) gene, TK gene, $\beta$-galactosidase gene, etc. The marker sequence may be any sequence known to those skilled in the art that serves these purposes, although typically the marker sequence will be a sequence encoding a protein that confers a selectable trait, such as an antibiotic resistance gene, or an enzyme that can be detected and that is not typically found in the cell. The marker sequence may also include regulatory regions such as a promoter or enhancer that regulates the expression of that protein. However, it is also possible to transcribe the marker using endogenous regulatory sequences. In one embodiment of the present invention, the marker facilitates separation of transfected from untransfected cells by fluorescence activated cell sorting, for example by the use of a fluorescently labeled antibody or the expression of a fluorescent protein such as GFP. Other DNA sequences that facilitate expression of marker genes may also be incorporated into the DNA constructs of the present invention. These sequences include, but are not limited to transcription initiation and termination signals, translation signals, post-translational modification signals, intron splicing junctions, ribosome binding sites, and polyadenylation signals, to name a few. The marker sequence may also be used to append sequence to the target gene. For example, it may be used to add a stop codon to truncate F-box translation. The use of selectable markers is well known in the art and need not be detailed herein. The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

A "mutated gene" or "mutation" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

As used herein, the term "nucleic acid" refers to polynucleotides such as deoxyribonucleic acid (DNA), and, where appropriate, ribonucleic acid (RNA). The should be understood to include either single- or double-stranded forms of nucleic acid, and, as equivalents, analogs of either RNA or DNA. Such nucleic acid analogs may be composed of nucleotide analogs, and, as applicable to the embodiment being described, may be single-stranded (such as sense or antisense) or double-stranded polynucleotides.

The phrase "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO: x refers to the complementary strand of the strand having SEQ ID NO: x or to any nucleic acid having the nucleotide sequence of the complementary strand of SEQ ID NO: x. When referring to a single stranded nucleic acid having the nucleotide sequence SEQ ID NO: x, the complement of this nucleic acid is a nucleic acid having a nucleotide sequence which is complementary to that of SEQ ID NO: x. The nucleotide sequences and complementary sequences thereof are always given in the 5' to 3' direction.

The phrase "operably linked" refers to functional linkage between a promoter and a second sequence, wherein the promoter sequence initiates transcription of RNA corresponding to the second sequence.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a, gap weight of 1, e.g., each amino acid gap is weighted as if it were a single amino acid or nucleotide mismatch between the two sequences.

The term "plant" includes whole plants, plant organs (e.g., leaves, stems, flowers, roots, etc.), seeds and plant cells and progeny of same. The class of plants which can be used in the method of the invention is as broad as the class of higher plants amenable to transformation techniques, including both monocotyledonous and dicotyledonous plants, as well as certain lower plants such as algae. It includes plants of a variety of ploidy levels, including polyploid, diploid and haploid. Useful crop plants of the invention include, but are not limited to, corn (*Zea mays*), *Brassica* spp. (e.g., canola (*B. napus*), *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

The term "plant" farther includes the following classes of plant species:

Dicotyledon (dicot): A flowering plant whose embryos have two seed halves or cotyledons. Examples of dicots are: tobacco; tomato; the legumes including alfalfa; oaks; maples; roses; mints; squashes; daisies; walnuts; cacti; violets; and buttercups.

Monocotyledon (monocot): A flowering plant whose embryos have one cotyledon or seed leaf. Non-limiting examples of monocots are: lilies; grasses; corn; grains, including oats, wheat and barley; orchids; irises; onions and palms.

"Lower plant", refers to a non-flowering plant including ferns, gymnosperms, conifers, horsetails, club mosses, liver warts, hornworts, mosses, red algae, brown algae, gametophytes, sporophytes of pteridophytes, and green algae.

In general, plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

The term "promoter" refers to a region of nucleic acid subsequences located upstream and/or downstream from the start of transcription which aid in the recognition, binding and/or initiation of RNA polymerase or other transcription proteins which initiate transcription of an associated gene. A "plant promoter" is a promoter capable of initiating transcription in plant cells. A "plant leucine aminopeptidase promoter" is a promoter derived from a leucine aminopeptidase gene, e.g., by cloning, isolating or recombinantly modifying a native promoter from a leucine aminopeptidase gene.

A "recombinant nucleic acid" comprises or is encoded by one or more nucleic acid which is derived from a nucleic acid which wag artificially constructed. For example, the nucleic acid can comprise or be encoded by a cloned nucleic acid formed by joining heterologous nucleic acids as taught, e.g., in Berger and Kimmel, Guide to Molecular Cloning Techniques, *Methods In Enzymology* Vol. 152 Academic Press, Inc., San Diego, Calif. (Berger) and in Sambrook et al. *Molecular Cloning-A Laboratory Manual* (2nd ed.) Vol. 1-3 (1989) (Sambrook) and in *Current Protocols In Molecular Biology*, Ausubel, F. M., et al., eds., Greene Publishing Associates, Inc. and John Wiley & Sons, Inc., (1996 Supplement) (Ausubel). Alternatively, the nucleic acid can be synthesized chemically.

As used herein, a "reporter gene construct" is a nucleic acid that includes a "reporter gene" operatively linked to a transcriptional regulatory sequences. Transcription of the reporter gene is controlled by these sequences. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences are recognized by effector molecules.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well, The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA, techniques, wherein generally, DNA encoding a specific polypeptide is inserted into a suitable expression vector which is in turn used to transform a host cell to produce the heterologous protein. Moreover, the phrase "derived from", with respect to a recombinant target gene, is meant to include within the meaning of "recombinant protein" those proteins having an amino acid sequence of a native target polypeptide, or an amino acid sequence similar thereto which is generated by mutations including substitutions and deletions (including truncation) of a naturally occurring form of the polypeptide.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express a recombinant F-box gene.

"Small molecule" as used herein, is meant to refer to a composition, which has a molecular weight of less than about 5 kD and most usefully less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate a target bioactivity.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a gene, most usefully a plant F-box gene.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

As used herein, the term "transfection" means the introduction of a nucleic acid, e.g., via an expression vector, into a recipient cell by nucleic acid-mediated gene transfer. Methods for transformation which are known in the art include any electrical, magnetic, physical, biological or chemical means. As used herein, "transfection" includes such specific techniques as electroporation, magnetoporation, $Ca^{++}$ treatment, injection, bombardment, retroviral infection and lipofection, among others. "Transformation" as used herein, refers to a process in which a cell's genotype is changed as a result of the cellular uptake of exogenous DNA or RNA, and, for example, the transformed cell expresses a recombinant form of a target polypeptide or, in the case of anti-sense expression from the transferred gene, the expression of a naturally-occurring form of the target polypeptide is disrupted.

As used herein, the term "transgene" means a nucleic acid sequence (encoding, e.g., one of the target polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic plant" refers to any plant, in which one or more of the cells of the plant contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, but rather is directed to the introduction of a recombinant DNA molecule. This molecule may be integrated within a chromosome, or it may be extrachromosomally replicating DNA. In the typical transgenic plants described herein, the transgene causes cells to express a recombinant form of one of the target polypeptides, e.g. either agonistic or antagonistic forms. However, transgenic plants in which the recombinant target gene is silent are also contemplated, as for example, FLP or CRE recombinant dependent constructs. Moreover, "transgenic plant" also includes those recombinant animals in which gene disruption of one or more plant genes is caused by human intervention, including both recombination and antisense techniques. A "transgenic plant" is, further, one which has been genetically modified to contain and express heterologous DNA sequences, either as regulatory RNA molecules or as proteins. As specifically exemplified herein, a transgenic plant is genetically modified to contain and express at least one heterologous DNA sequence operably linked to and under the regulatory control of transcriptional control sequences which function in plant cells or tissue or in whole plants. As used herein, a transgenic plant also refers to progeny of the initial transgenic plant where those progeny contain and are capable of expressing the heterologous coding sequence under the regulatory control of the plant-expressible transcription control sequences described herein. Seeds containing transgenic embryos are encompassed within this definition, as are cuttings and other plant materials for vegetative propagation of a transgenic plant.

When plant expression of a heterologous gene or coding sequence of interest is desired, that coding sequence is operably linked in the sense orientation to a suitable promoter and advantageously under the regulatory control of DNA sequences which quantitatively regulate transcription of a downstream sequence in plant cells or tissue or in plants, in the same orientation as the promoter, so that a sense (i.e., functional for translational expression) mRNA is produced. A transcription termination signal, for example, as polyadenylation signal, functional in a plant cell is advantageously placed downstream of the metal or organometal resistance coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. In the present invention, the mercury resistance coding sequence can serve as a selectable marker for transformation of plant cells or tissue. Where constitutive gene expression is desired, suitable plant-expressible promoters include the 35S or 19S promoters of Cauliflower Mosaic Virus, the nos, acs or mas promoters of *Agrobacterium tumefaciens* Ti plasmids, and others known to the art. Where tissue specific expression of the plant-expressible metal resistance coding sequence is desired, the skilled artisan will choose from a number of well-known sequences to mediate that form of gene expression. Environmentally regulated promoters are also well known in the art, and the skilled artisan can choose from well known transcription regulatory sequences to achieve the desired result.

"Transcriptional regulatory sequence" is a generic term used throughout the specification to refer to DNA sequences, such as initiation signals, enhancers, and promoters, which induce or control transcription of protein coding sequences with which they are operably linked. In some embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the protein.

The term "vector" refers to a nucleic acid molecule capable of transporting another nucleic acid to which it has been linked. One type of useful vector is an episome, i.e., a nucleic acid capable of extra-chromosomal replication. Particularly useful vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

F-box Nucleic Acid and Polypeptide Sequences

The F-box nucleic acid and protein sequences of the invention include the *Arabidopsis thaliana* F-Box protein:

DNA SEQUENCE OF *ARABIDOPSIS THALIANA* F-BOX PROTEIN:
GENBANK ACCESSION NO. NM-111499 (SEQ ID NO. 2))

| | |
|---|---|
| 1 | TTTTTCAAAT CAAATCAGAA TACATTGATT CTGTATATCT TATTGAAAAA TCCATCAATT |
| 61 | TACATCAACA ATTTTATATC TAATAATTAA TTTAAAGAGA AAATTTATAA AAGTTTATTA |
| 121 | GAGCA11ATAA CTCAAACTCG GATTTTATAG TCGTTATGAC CCGGTTTGAC TATTGAACCG |
| 181 | TTTAACCGAG ARATTGGGAC TCAATTAAGA CAACCGAAAC TAGACCCGGA TCCAGTGTTA |
| 241 | GCGGGCTAGA TTAAGGTGTC GGGTCATAGC GGAGAAGCAA CCAGACGCCA ACAAAAAAG |
| 301 | CGATCCAGTT GCTGTGGGAA GCGATAATGG AGGCGACGAA GAGAGAAAGA CGGAGAGAAG |
| 361 | ATGACGACGG CGAAAAAGCT TCACCGGAAT CACTCGTTCT TCCACCAGAG ATCATTACAG |
| 421 | AAATTCTTCT CCGATTACCA GCCAAATCGA TCGGGCGATT CAGGTGCGTA TCAAAGCTCT |
| 481 | TTTGCACTTT ATCGTCAGAT CCAGGGTTCG CGAAGATTCA CCTCGATCTG ATCCTTCGM |

-continued

| | |
|---|---|
| 541 | ACGRATCCGT AAGATCGCTC CACCGTAAGC TCATTGTGTC TTCACATAAT CTGTACTCGT |
| 601 | TAGATTTCAA TTCGATCGGT GACGGAATTA GGGATTTAGC GGCTGTGGAA CACAATTATC |
| 661 | CTCTTAAAGA CGATCCAAGC ATTTTCTCTG AGATGATTAG GAATTACGTG GGGGACCATC |
| 721 | TGTACGATGA TCGTCGCGTG ATGCTTAAGC TGAATGCGAA ATCGTATCGA AGAAACTGGG |
| 781 | TTGAGATCGT TGGATCTTCC AATGGTTTAG TGTGTATCTC TCCTGGTGAA GGAGCTGTTT |
| 841 | TCTTGTATAA TCCAACTACC GGAGATTCCA AGAGATTACC TGAAMATTTT CGTCCCAAAT |
| 901 | CTGTAGAATA CGAAAGAGAT AATTTCCAAA CTTATGGATT TGGTTTCGAT GGTCTCACTG |
| 961 | ATGATTACAA ATTGGTGAAG CTTGTTGCTA CCAGTGAAGA TATTCTCGAT GCTAGTGTCT |
| 1021 | ATTCCTTGAA GGCTGACTCA TGGAGACGGA TCTGCAATTT GAATTATGAG CACAACGATG |
| 1081 | GCTCCTACAC GTCCGGTGTG CATTTCAACG GTGCGATTCA CTGGGTGTTC ACAGAGAGTA |
| 1141 | GGCACAACCA AAGAGTGGTT GTAGCATTTG ATATTCAAAC CGAGGAGTTT CGAGAGATGC |
| 1201 | CAGTGCCTGA TGAAGCTGAA GATTGTTCCC ATAGGTTTAG CAACTTTGTG GTCGGAAGTC. |
| 1261 | TCAATGGACG TCTCTGTGTG GTCAATAGTT GCTACGATGT GCATGATGAT ATATGGGTGA |
| 1321 | TGAGTGAGTA CGGTGAAGCT AAATCCTGGA GCAGAATTCG AATCAACTTG TTGTATAGGT |
| 1381 | CGATGAAACC GCTCTGTTCG ACTAAGAACG ATGAAGAGGT TCTTCTGGAG CTTGATGGAG |
| 1441 | ACCTGGTGTT GTACAACTTT GAAACCAATG CATCGAGTAA TCTAGGAATT TGTGGGGTTA |
| 1501 | AGCTCAGTGA CGGGTTCGAG GCAAATACAT ACGTAGAGAG CCTCATATCA CCCAACTClT |
| 1561 | ATGGTATAGA GAGCTGAGGA AGTCTGCTTT TGCTAAGAT ATAATAAACC AACATTCGGA |
| 1621 | TTAGAAATGT TTTAGAAACA TAATCATGTA ATATGTATCA TGTAATTAAC AACGAATGGT |
| 1681 | CAATGGGTAT TTTAAGTTTC TTTCTCCT and, |

| POLYPEPTIDE SEQUENCE OF *ARABIDOPSIS THALIANA* F-BOX PROTEIN (GENBANK ACCESSION NO. NR-566277 (SEQ ID NO. 1)) | |
|---|---|
| 1 | MKAIQLLWEA IMEATKRERR REDDDGEKAS PESLVLPPEI ITEILLRLPA KSIGRFRCVS |
| 61 | KLFCTLSSDP GFAKIHLDLI LRNESVRSLH RKLIVSSHNL YSLDFNSIGD GIRDLVEH |
| 121 | NYPLKDDPSI FSEMIRNYVG DHLYDDRRVM LKLNAKSYRR NWVEIVGSSN GLVCISPGEG |
| 181 | AVFLYNPTTG DSKRLPENFR PKSVEYERDN FQTYGFGFDG LTDDYKLVKL VATSEDILDA |
| 241 | SWSLKADSW RRICNLNYEH NDGSYTSGVH FNGAIHWVFT ESRHNQRWV AFDIQTEEFR |

```
301  EMPVPDEAED CSHRFSNFW GSLNGRLCW NSCYDVHDDI WVMSEYGEAK
     SWSRIRINLL

361  YRSMKPLCST KNDEEVLLEL DGDLVLYNFE TNASSNLGIC GVKLSDGFEA
     NTYVESLISP

421  NSYGIES
```

Other equivalent nucleic acids and polypeptides include those discernable from the following summary of this F-box protein family (At3g06240).

SELECTED PROTEIN SIMILARITIES

Comparison of sequences in UniGene with proteins supported by a complete genome. The alignments can suggest function of a gene.

*A. thaliana* ref:NP_566277.1—expressed protein [*Arabidopsis thaliana*] 100%/416 aa (see ProtEST)

GENE EXPRESSION

Tissues and development stages from this gene's sequences survey gene expression. Links to other NCBI expression resources.

cDNA sources: mixture of silique and flower; green siliques; roots; seed; adult vegetative tissue; flower buds; flowers and buds; inflorescence lacking open or older flowers.

GEO profiles: Gene expression profiles in the NCBI Gene Expression Omnibus database.

MAPPING POSITION

Genomic location specified by transcript mapping, radiation hybrid mapping, genetic mapping or cytogenetic mapping.

*Arabidopsis* Chromosome: III

SEQUENCES

Sequences representing this gene; mRNAs, ESTs, and gene predictions supported by transcribed sequences.

NM_111499.3 *Arabidopsis thaliana* F-box family protein (At3g06240) mRNA, complete cds P AY084423.1 *Arabidopsis thaliana* clone 108003 mRNA, complete sequence P AK118303.1 *Arabidopsis thaliana* At3g06240 mRNA for unknown protein, complete cds, clone: RAFL19-58-P14 P BT006048.1 *Arabidopsis thaliana* clone U50970 putative F-box protein family (At3g06240) mRNA, complete cds P BX824678.1 *Arabidopsis thaliana* Full-length cDNA Complete sequence from clone GSLTPGH64ZA06 of Hormone Treated Callus of strain col-0 of *Arabidopsis* thaliana (thale cress) P BX829355.1 *Arabidopsis thaliana* Full-length cDNA Complete sequence from clone GSLTSIL94ZF11 of Silique of strain col-0 of *Arabidopsis thaliana* (thale cress) P EST Sequences (19) BP842389.1 Clone RAFL21-54-K05 5' read BP825839.1 Clone RAFL22-69-O13 mixture of silique and flower 5' read BP824403.1 Clone RAFL22-09-H01 mixture of silique and flower 5' read BP817574.1 Clone RAFL22-45-F24 mixture of silique and flower 5' read BP652696.1 Clone RAFL19-94-A01 mixture of silique and flower 3' read BP644487.1 Clone RAFL19-65-J12 mixture of silique and flower 3' read BP643288.1 Clone RAFL19-61-H05 mixture of silique and flower 3' read CF773451.1 Clone 17B03 inflorescence lacking open or older flowers BX838532.1 Clone GSLTFB50ZF02 flowers and buds 5' read P BX836858.1 Clone GSLTLS79ZF01 adult vegetative tissue 5' read BX837508.1 Clone GSLTLS79ZE01 adult vegetative tissue 5' read P AU239163.1 Clone RAFL19-58-P14 mixture of silique and flower 5' read P AU230440.1 Clone RAFL19-58-P14 mixture of silique and flower 3' read AV562416.1 Clone SQ169f12F green siliques 3' read A AV551881.1 Clone RZ15g09R roots 5' read AV540406.1 Clone RZ15g09F roots 3' read P AV534311.1 Clone FB078a02F flower buds 3' read P BE525819.1 Clone 600034345R1 seed 5' read BE523193.1 Clone M35B4 seed 5' read P.

Homologous F-box Proteins

The invention further provides F-box protein encoding genes that are homologous to those specifically described herein (e.g., the *Arabidopsis thaliana* F-box Protein shown above as SEQ ID NO: 1, and the corresponding encoding sequence shown above as SEQ ID NO: 2). For example, equivalent nucleotide sequences include sequences that differ by one or more nucleotide substitutions, additions or deletions, such as intragenus variants; and also include sequences that differ from the nucleotide sequence encoding the portion of a protein represented herein due to the degeneracy of the genetic code. Equivalent nucleic acids also include nucleotide sequences that hybridize under stringent conditions (i.e., equivalent to about 20-27° C. below the melting temperature (Tm) of the DNA duplex formed in about 1 M salt) to a nucleotide sequence of an heterologous gene of the invention.

Particularly useful nucleic acids encode polypeptides comprising an amino acid sequence which is at least 70% identical, 80% identical or 85% identical with an amino acid sequence of the invention. Nucleic acids encoding polypeptides, particularly polypeptides retaining an activity of one of the subject heterologous genes which confer an F-box activity, and comprising an amino acid sequence which is at least about 90%, or at least about 95%, and most usefully at least about 98-99% identical with an amino acid sequence of the invention are also within the scope of the invention.

Another aspect of the invention provides nucleic acid that hybridizes under high or low stringency conditions to nucleic acid which encodes a polypeptide identical or homologous with an amino acid sequence of the invention. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989) 6.3.1-6.3.6. For example, the salt concentration in the wash step can be selected from a low stringency of about 2.0.×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding an heterologous protein of the present invention, yet which differ from the nucleotide sequences referenced herein due to degeneracy in the genetic code, are also within the scope of the invention. Such nucleic acids are understood to be capable of encoding functionally equivalent polypeptides (i.e., a polypeptide having at least a portion of the biological activity of a protein encoded by the enumerated sequences). For instance, a number of amino acids are designated by more than one triplet. Codons that specify the same amino acid (for example, CAU and CAC are synonyms for histidine) may result in "silent" mutations which do not affect the amino acid sequence of the protein. However, it is expected that DNA sequence polymorphisms that do lead to changes in the amino acid sequences of the protein will exist even within the same species. One skilled in the art will appreciate that these variations in one or more nucleotides (up to about 3-4% of the nucleotides) of a gene encoding a protein may exist among individual cells of a given species, e.g., amongst a population of *Arabidopsis thaliana* cells, due to natural allelic variation. Any and all such nucleotide variations and resulting amino acid polymorphisms are within the scope of this invention.

Fragments of the nucleic acid encoding portions of the subject heterologous F-box such as a fragments which retain the ability to interact with the ubiquitin proteolytic pathway, are also within the scope of the invention. As used herein, such fragments refer to nucleotide sequences having fewer nucleotides than the coding sequence of the gene, yet still include enough of the coding sequence so as to encode a polypeptide with at least some of the activity of the full-length protein activity.

In yet a further embodiment, the recombinant regulatory genes may further include, additional nucleotide sequences. For instance, the recombinant gene can include nucleotide sequences of a PCR fragment generated by amplifying the gene from a genomic DNA library, e.g., 5' and 3' non-coding sequences of either of the subject genes.

Nucleic acids within the scope of the invention may also contain linker sequences, modified restriction endonuclease sites and other sequences useful for molecular cloning, expression or purification of the recombinant polypeptides.

As indicated by the examples set out below, a nucleic acid encoding one of the subject proteins may be obtained from mRNA present in a sample of eukaryotic cells, such as those of a vascular plant. It will also be possible to obtain nucleic acids encoding the subject proteins from genomic DNA obtained from such cells. For example, a gene encoding one of the subject F-box proteins can be cloned from either a cDNA or a genomic library from other plant species in accordance with protocols described herein, as well as those generally known in the art. For instance, a cDNA encoding an heterologous protein can be obtained by isolating total mRNA from a plant, generating double stranded cDNAs from the total mRNA, cloning the cDNA into a suitable plasmid or bacteriophage vector, and isolating clones expressing the subject protein using any one of a number of known techniques, e.g., oligonucleotide probes, western blot analysis, or complementation. Genes encoding related proteins can also be cloned using established polymerase chain reaction techniques in accordance with the nucleotide sequence information provided by the invention. The nucleic acid of the invention can be DNA or RNA.

Moreover, the nucleotide sequence determined from the cloning of the subject heterologous genes will permit the generation of probes designed for use in identifying the heterologous transgenic DNA as well as for detecting the presence of the corresponding heterologous mRNA. For example, the subject nucleic acids may be used following transgenic targeting to confirm the presence and integrity of the introduced sequence as well as the amount and specificity of expression in transgenic progeny. For instance, the present invention provides a probe/primer comprising a substantially purified oligonucleotide, wherein the oligonucleotide comprises a region of nucleotide sequence which hybridizes under stringent conditions to at least 10, 25, 50, or 100 consecutive nucleotides of sense or anti-sense sequence of one of the subject nucleic acids, or naturally occurring mutants thereof. In some embodiments, the probe/primer further comprises a label group attached thereto and able to be detected, e.g. the label group is selected from the group consisting of radioisotopes, fluorescent compounds, enzymes, and enzyme co-factors.

Other F-Box Proteins

Still other F-box proteins for use in the invention are known in the art and specifically described elsewhere (see, e.g., U.S. Pat. Nos. 6,573,094 and 6,232,081, the contents of each of which are hereby incorporated by reference in their entireties). Other known plant F-box proteins include the F-box protein TIR1, an auxin receptor (see Dharmasiri et al. (2005) *Nature* 435: 441-5; GenBank Accession No. Q57000; GI: 68053009)), as well as three additional F-box proteins, teemed AFB1, 2, and 3, which also regulate auxin response (see Dharmasiri et al. (2005) *Dev. Cell* 9:109-119). Indeed, the *Arabidopsis* genome alone encodes nearly 700 F-box proteins (see Gagne et al. (2002) *Proc. Natl. Acad. Sci. USA* 99: 11519-24). Still other plant F-box proteins are known in the art and available to the skilled artisan using only routine methods in gene cloning.

Vectors

This invention also provides expression vectors which include a nucleotide sequence encoding one of the subject polypeptides and operably linked to at least one regulatory sequence. Operably linked is intended to mean that the nucleotide sequence is linked to a regulatory sequence in a manner which allows expression of the nucleotide sequence. Plant egulatory sequences are art-recognized. Accordingly, the term regulatory sequence includes promoters, enhancers and other expression control elements. Exemplary plant regulatory sequences are described in Yusibo et al, (1999) *Curr. Top. Micro. Immun.* 240: 81-94 and Hood et al. (1999) *Adv. Exp. Med. Biol.* 464: 127-47. For instance, any of a wide variety of expression control sequences-sequences that control the expression of a DNA sequence when operatively linked to it may be used in these vectors to express DNA sequences encoding the Zostera genetic trait-conferring proteins and nucleic acids of this invention. Such useful expression control sequences, include, for example, the constitutive maize ubiquitin promoter (ubi promoter) (Christensen et al. (1992) *Plant Mol. Biol.* 18: 675-89; Cornejo et al. (1993) *Plant Mol. Biol,* 23: 567-81) and the potato PinII terminator sequence (An et al. (1989) *Plant Cell* 1: 115-22). Other useful expression control sequences are those derived from plant viruses such as: the 35S promoter, which is derived from Cauliflower Mosaic Virus sequences; and the TMV coat protein promoter, such as that contained in the cloning vector designated "30B" which is derived from the Tobacco Mosaic Virus. Also included in certain aspects of the invention are non-plant transcriptional regulatory sequences such as early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding beta-glucuronidase (Jefferson (1987) *Plant Mol. Biol. Rep.* 5:387-405), luciferase (Ow et al. (1986) *Sci.* 234: 856-859), B and C1 gene products that regulate anthocyanin pigment production (Goffet et al. (1990) *EMBO J* 9:2517-2522).

The present invention may also utilize the *Agrobacterium* system for transforming plants, the recombinant DNA constructs additionally comprise at least the right T-DNA border sequence flanking the DNA sequences to be transformed into plant cell. In some embodiments, the sequences to be transferred in flanked by the right and left T-DNA border sequences. The proper design and construction of such T-DNA based transformation vectors are well known to those skilled in the art.

This invention also pertains to a host cell transfected with a recombinant gene in order that it may express a recombinant protein of the present invention. The host cell may be any prokaryotic or eukaryotic cell. For example, a plant F-box protein of the present invention may be expressed in bacterial cells, such as *E. coli*, insect cells, yeast, or mammalian cells. Other suitable host cells are known to those skilled in the art, Another aspect of the present invention concerns recombinant forms of the subject plant proteins. The term "recombinant protein" refers to a protein of the present invention which is produced by recombinant DNA techniques, wherein generally DNA encoding the protein is inserted into a suitable expression vector which is in turn used to transform a host cell to produce the heterologous protein. Moreover, the phrase "derived from", with respect to a recombinant gene encoding one of the subject proteins, is meant to include within the meaning of "recombinant protein" those proteins having an amino acid sequence of the native (or "authentic") form of the plant protein, or an amino acid sequence similar thereto, which is generated by mutation so as to include substitutions and/or deletions relative to a naturally occurring form of the protein. To illustrate, recombinant proteins particularly useful in the present invention, in addition to those having an amino acid sequence of the native proteins, are those recombinant proteins having amino acid sequences which are at least 70% homologous, or 80% homologous and most usefully 90% homologous with an amino acid sequence of the present invention. A polypeptide which having an amino acid sequence that is at least about 95%, or at least about 98%, and most usefully identical to one of the polypeptide sequences of the invention are also within the scope of the invention. Thus, the present invention pertains to recombinant proteins which are derived, for example from *Arabidopsis thaliana* F-box genes and which have amino acid sequences evolutionarily related to a sequence encoded by an orthologous gene from another plant protein, wherein "evolutionarily related to" refers to polypeptides having amino acid sequences which have arisen naturally (e.g. by allelic variance), as well as mutational variants of the regulatory proteins which are derived, for example, by combinatorial mutagenesis.

Transgenic Plants and Plant Cells

Techniques for stably incorporating genetic constructs into the genome of target plants are well known in the art and include *Agrobacterium tumefaciens*-mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology (as described, for example by Bevan, (1984) *Nucl. Acids Res.* 12:8711-8721). Targets for the introduction of the genetic constructs of the present invention include tissues, such as leaf tissue, dissociated cells, protoplasts, seeds, embryos, meristematic regions; cotyledons, hypocotyls, and the like.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al. Somatic embryogenesis in woody plants as described in Thorpe, T. A. ed., *In Vitro Embryogenesis of Plants*. Vol. 20 in *Current Plant Science and Biotechnology in Agriculture*, Chapter 12, pp. 471-540, 1995. Specific protocols for the regeneration of spruce are discussed by Roberts et al., Somatic Embryogenesis of Spruce is described in: Synseed *Applications of synthetic seed to crop improvement*. Redenbaugh, K, ed., CRC Press, Chapter 23, pp. 427-449, 1993. The resulting transformed plants may be reproduced sexually or asexually, using methods well known in the art, to give successive generations of transgenic plants.

As discussed above, the production of RNA in target plant cells can be controlled by choice of the promoter sequence. A target plant may be transformed with more than one genetic construct of the present invention, thereby modulating the activity of more than one polypeptide, affecting polypeptide activity in more than one tissue, or affecting polypeptide activity at more than one expression time. Similarly, a genetic construct may be assembled containing more than one open reading frame coding for an inventive polypeptide or more than one non-coding region of a gene coding for such a polypeptide. The polynucleotides of the present invention may also be employed in combination with other known sequences encoding polypeptides involved in plant cell signaling.

The isolated polynucleotides of the present invention may be employed as probes to isolate other related F-box DNA sequences, including those from other plant species, using techniques well known to those of skill in the art, such as routinely used DNA hybridization and PCR techniques.

The inventive polynucleotides, polypeptides and antibodies to such polypeptides may be used to screen for molecules that interact with such polynucleotides and/or polypeptides and that thereby modulate cell signaling. Techniques for performing such assays are well known in the art. Similarly, the polynucleotides and polypeptides of the present invention may be employed in studies designed to elucidate the mechanism of cell signaling pathways.

The invention provides numerous methods for the transformation of plants with an heterologous F-box gene or genes which contribute to the production of oils in the recipient plant, the details of which methods are further described below. In some embodiments, the heterologous gene is introduced by transformation, and the introduced gene is expressed stably over the life of the plant and is further capable of being transmitted to the plant's offspring. In general, it is desirable for the transgene to be integrated into the nuclear DNA, although the plastid genome may be an appropriate target for some constructs.

The transformation of crop and other plants can be effected by a number of methods known in the field of plant biotechnology. The method for transformation will vary with the plant species to be transformed and the desired pattern and stability of transgene expression. For example, particle bombardment methods have been shown to be effective in transforming many plant species, including those previously considered recalcitrant to transformation. This method is commonly used in the transformation of monocotyledonous plants such as corn. Another plant transformation method available is *Agrobacterium*-mediated gene transfer, which is commonly used to transform dicotyledonous crops.

Still other methods available for plant transformation do not rely upon tissue culture for the recovery of transgenic plants, thereby allowing the production of transgenics from plant species for which no reliable method of tissue culture exists. For example, microtargeting of particle-bound DNA into shoot meristematic tissue produces transgenic flowering parts from which transgenic seeds arise (Sautter et al. (1991) *Biotech*. 9: 1080-85). Transgenic seeds can also be created by electrophoresing DNA into meristematic tissue (Griesbach (1994) *Plant Sci*. 102: 81-89; Burchi et al. (1995) *J Genetl Breeding* 49: 163-8). This method has proven successful in the transformation of several plant species including orchids, chrysantehemums, carnations, lisianthus, peppers, and even woody plant species such as plum (*Plumus domestica*).

In general, the invention provides methods and reagents for the genetic engineering of a target host plant, such as a crop plant, with an heterologous nucleic acid which encode an F-box protein function that contributes to the production of oils in the recipient plant. One method for transformation makes use of the aforementioned common soil bacterium *Agrobacterium* (see Birch (1997) *Ann. Rev. Plant Physiol. Plant Mol. Biol*. 48: 297-326). This method involves a modified transfer-DNA (T-DNA) vector which carries the desired nucleic acid fragment between the T-DNA border regions (specific 25 base pair direct repeat regions), The resulting vector is transferred into an *Agrobacterium* host and the target host plant is inoculated with the transformed recombinant bacterium. Virulence genes products of *Agrobacterium* then actively recognize, excise, transport, and integrate the T-DNA region into the host plant genome.

*Agrobacterium tumefaciens*-mediated transformation techniques, including disarming and use of binary vectors, are well described in the scientific literature (see, e.g. Horsch, et al. (1984) *Science* 233:496-8, and Fraley, et al (1983) *Proc. Nat. Acad. Sci. USA* 80:4803, *Agrobacterium*-mediated transformation is a particularly useful method of transformation of dicots.

The natural host range of *Agrobacterium* is limited and so this approach to transformation is not practicable in some target host plants, particularly cereal crops and other monocotyledonous species. For such crops, the invention provides alternative approaches to transformation such as direct uptake of naked DNA into protoplasts or tissues using electroporation or particle gun bombardment. In this method, the cotransformation of a selectable marker gene along with the gene of interest allows the preferential growth of the transformed cells in cell culture. Successive manipulations of the chemical composition of the culture medium, especially the plant hormones, allows the regeneration of complete plants. This method has allowed the recovery of genetically engineered plants in virtually all crop plants.

One representative method for direct transformation of the transgene construct is by particle bombardment of target plant tissues with high-velocity microprojectiles (see, e.g., Finer et al. (1999) *Curr. Top. Micro. and Immun*. 240: 60-80 for review). This method utilizes a particle accelerator or "gene blaster" to penetrate the outer surface layers of the plant tissue or protoplast (Sanford (1988) *Trends Biotech*. 1 6: 299-302). Biolistics, a combination of "biological" and "ballistics", describes a technique which utilizes instrumentation to accelerate DNA coated microprojectiles into cells, past the cell wall and cell membrane. The microprojectile is generally small enough (0.5-5.0 mm) to enter the plant cell without too much damage, yet large enough to have the mass to penetrate the cell wall and carry an appropriate amount of DNA on its surface into the interior of the plant cell.

A number of different particle gun designs may be used. The basis of all of these designs is to coat the DNA onto small dense particles and accelerate the particles towards a target tissue. The particles usually consist of either gold or tungsten spherical particles which are between 0.5 and 5.0 mm in diameter. Gold particles are chemically inert, generally more uniform in size than tungsten particles and produce no cytootoxic effects. Accordingly, gold particles are generally more effective than tungsten particles. Ideally the particles used for bombardment should have good initial affinity for DNA, yet freely release the DNA once inside the target cell cytoplasm or nucleus.

To prepare DNA-coated microprojectiles, washed gold or tungsten particles are mixed with plasmid DNA. The DNA is bound on the particles using either ethanol or calcium chloride precipitation methods, which are known in the art. Spermidine may be added to the mixture, possibly protecting the DNA from degradation and/or altering its conformation. After precipitation, the particles may be washed, resuspended and either dried or stored on ice as an aqueous suspension until needed.

The particle gun may utilize a macrocarrier, which supports or carries the particles and is accelerated along with the particles towards the target. The macrocarrier is usually retained by a stopping plate or screen before it collides with the target, whereas the particles continue along their course. In most cases, the particles are accelerated under partial vacuum in a vacuum chamber to reduce air drag. Particle penetration is controlled by modifying the intensity of the explosive burst, by changing the distance that the particles must travel to reach the target tissue or by using different sized particles. A commercial hand-held device (the Helios Gene Gun) is available from BioRad Laboratories (Hercules, Calif.). A helium-modified bombardment device, which utilizes continual build-up of helium back-pressure delivered to a calibrated rupture disc which transmits a shock wave to a second disc or macrocarrier that holds the DNA-coated particles, is also available from BioRad (i.e. the PDS-1000/He unit). A high voltage electrical discharge gun which causes rapid vaporization of a water droplet which in turn transmits a shock wave to a mylar sheet coated with DNA-bound particles has also been developed (see McCabe and Christou (1993) *Plant Cell Tiss. Organ. Cult.* 33: 227-236). Yet another device for particle bombardment is a microtargeting device, which does not utilize a macrocarrier (Sautter et al. (1991) *Bio/Technology* 9: 1080-5). This device accelerates small amounts of a DNA/particle mixture in a focused stream of high-pressure nitrogen. The DNA is not precipitate on the gold particles, but is delivered as a mixture.

A variety of different plant tissues have been used as targets for particle bombardment-mediated transformation. Selection of the appropriate target tissue is dependent on multiple factors. For rapid gene expression analysis, various plasmid constructs can be introduced into different tissues and transient expression can be quickly analyzed to assess promoter activity without the production of stably transformed plants (see e.g. Iida et al. (1995) *Plant Cell Rep.* 14: 539-44). Almost any tissue can be used for transient expression studies as long as the cell wall is penetrable by the DNA-coated particles. For example, embryogenic plant cell cultures have been used successfully for the production of transformed plants (see e.g. Fromm et al. (1990) *Bio/Technology* 8: 833-9). Shoot apical meristem transformation results in chimeric plants, where the transformed cells directly give rise to germ-line tissue and the introduced DNA is then passed onto progeny plants. Bombardment of shoot meristematic tissues followed by tissue culture expansion of the transformed cells has been used to produce genetically-transmissible transgenic plant lines (McCable et al. (1988) *Bio/Technology* 6: 923-6). In addition to embryogenic cultures and shoot tips, other tissues that have been subjected to particle bombardment include leaves (Klein et al. (1988) *Proc. Nat. Acad. Sci.* USA 85: 8502-5), root sections (Seki et al. (1991) *Appl. Microbiol. Biotech.* 36: 228-30), stem sections (Loopstra et al. (1992) *Can. J. Res.* 22: 993-6), pollen (Twell et al. (1989) *Plant Physiol.* 91-1270-4), styles (Clark and Sims (1994) *Plant Physiol.* 106: 25-36), cereal aleurone cells (Kim et al. (1992) *Mol. Gen. Genet.* 232: 383-93) and tassel primordia (Dupeuis and Pace (1993) *Plant Cell Rep.* 12: 607-11). In certain instances, the plant tissue that is selected for particle bombardment-mediated transformation be relatively new, as long-term cell cultures can result in abnormalities that may compromise the usefulness of the transgenic plant—such as infertility of the subsequent transgenic progeny (see Rhodes et al. (1988) *Biotech.* 6: 56-60).

In certain instances, the magnitude of transgene expression varies markedly with the site of insertion and the nature of the inserted sequence(s). For example, while T-DNA mediated transfer typically results in the insertion of a single complete intact DNA fragment at a single locus, direct DNA transfer approaches frequently result in long concatamers of the transferred DNA (see e.g. Czernilofsky et al. (1986) *DNA* 5: 473-82). Such multiple tandem insertions are associated with transcriptional "silencing" phenomena in certain instances. Furthermore, the site of insertion within the plant genome frequently affects the strength of expression of the transgene—a phenomenon know as "position effect." Accordingly, the invention provides methods for mitigating interference with the expression of the transgene. For example, position effects can be mitigated by flanking transgenes with specific matrix-associated regions which insulate transcriptional regulation from the effects of surrounding chromatin (see, e.g., Mlynarova et al. (1994) *Plant Cell* 7: 599-609). For example, scaffold attachment regions (SARs, also known as matrix attachment regions or MARs) may be included in the transgene vector construct. Usefully, the SARs are ligated to the flanking regions of the gene of interest. These sequences are known in the art (e.g. a tobacco SAR is described in Breyne et al. (1992) *Plant Cell* 4: 463-71; and Allen et al. (1996) *Plant Cell* 8: 899-913). Furthermore, transgene silencing mediated by homology-dependent processes can be avoided by utilizing transgenic plant lines which avoid multiple tandem or inverted repeat insertion patterns, and by limiting homology of the inserted transgene with any corresponding endogenous host gene(s) by engineering conserved codon replacements within the transgene construct where appropriate. When the transgene is inserted as one intact DNA fragment at a single locus, its expression generally behaves in a highly consistent manner. Such transgenic loci exhibit the expected additive gene action both within loci (hemizygous versus homozygous) and between loci (dihybrids between homozygous transgenic individuals). Loss of transgene unction is rare in such transgenic lines (approximately one in ten thousand), which is consistent with the performance of many endogenous plant genes. Optimized transgenic plants of the invention may be obtained by screening candidate plants for persistent expression of the transgene through multiple generations of breeding or rounds of vegetative propogation.

EXAMPLES

The following examples are offered by way of illustration and not by way of limitation.

Materials and Methods

AT3G06240: F-box family protein, contains F-box domain Pfam:PF00646

PRIMERS for the original PCR date Feb. 28, 2002

```
Forward primer (Fbox-For)
5'-CAC CAA ACA ATG GAG GCG ACG AAG AGA G-3'

Reverse primer (Fbox-Rev_1)
5'-ATC TTA GCA AAA AGC AGA CTT C-3'
```

These primers were used to successfully RT-PCR the following sequence.

<u>CACC AAACA</u> ATGGAGGCGACGAAGAGAGAAAGACGGA

GAGAAGATGACGACGGCGAAAAAGCTTCACCGGAATCACTCGTTCTTCCACCAGAGATCA

TTACAGAAATTCTTCTCCGATTACCAGCCAAATCGATCGGGCGATTCAGGTGCGTATCAA

-continued
```
AGCTCTTTTGCACTTTATCGTCGGATCCAGGGTTCGCGAAGATTCACCTCGATCTGATCC

TTCGAAACGAATCCGTAAGATCGCTCCACCGTAAGCTCATTGTGTCTTCACATAATCTGT

ACTCGTTAGATTTCAATTCGATCGGTGACGGAATTAGGGATTTAGCGGCTGTGGAACACA

ATTATCCTCTTAAAGACGATCCAAGCATTTTCTCTGAGATGATTAGGAATTACGTGGGGG

ACCATCTGTACGATGATCGTCGCGTGATGCTTAAGCTGAATGCGAAATCGTATCGAAGAA

ACTGGGTTGAGATCGTTGGATCTTCCAATGGTTTAGTGTGTATCTCTCCTGGTGAAGGAG

CTGTTTTCTTGTATAATCCAACTACCGGAGATTCCAAGAGATTACCTGAAAATTTTCGTC

CCAAATCTGTAGAATACGAAAGAGATAATTTCCAAACTTATGGATTTGGTTTCGATGGTC

TCACTGATGATTACAAATTGGTGAAGCTTGTTGCTACCAGTGAAGATATTCTCGATGCTA

GTGTCTATTCCTTGAAGGCTGACTCATGGAGACGGATCTGCAATTTGAATTATGAGCACA

ACGATGGCTCCTACACGTCCGGTGTGCATTTCAACGGTGCGATTCACTGGGTGTTCACAG

AGAGTAGGCACAACCAAAGAGTGGTTGTAGCATTTGATATTCAAACTGAGGAGTTTCGAG

AGATGCCAGTGCCTGATGAAGCTGAAGATTGTTCCCATAGGTTTAGCAACTTTGTGGTCG

GAAGTCTCAATGGACGTCTCTGTGTGGTCAATAGTTGCTACGATGTGCATGATGATATAT

GGGTGATGAGTGAGTACGGTGAAGCTAAATCCTGGAGCAGAATTCGAATCAACTTGTTGT

ATAGGTCGATGAAACCGCTCTGTTCGACTAAGAACGATGAAGAGGTTCTTCTGGAGCTTG

ATGGAGACCTGGTGTTGTACAACTTTGAAACCAATGCATCGAGTAATCTAGGAATTTGTG

GGGTTAAGCTCAGTGACGGGTTCGAGGCAAATACATACGTAGAGAGCCTCATATCACCCA

ACTCTTATG GTATAGAGAGCTGA GGAAGTCTGCTTTTTGCTAAGAT
```

One of the purified PCR products, Fbox_like1, was then cloned into GATEWAY pENTR/D-TOPO vector. This was designated as "Entry Clone" and was used to sub-clone the desired sequence in to GATEWAY expression vectors (Invitrogen, Carlsbad, Calif. cat.number pENTRID-TOPO, K240020). Further sequence information is available from Invitrogen.

One of the Fbox entry clone plasmids was chosen for full length sequencing (coded Fbox-like-LIG1). The clone was sequenced completely using internal primers as well and was found to be full-length and without PCR errors.

Sub-cloning the Fbox-like1 gene fragment to the GATEWAY expression vector pGATE-Phas is shown in FIG. 10. The vector was constructed by inserting Gateway Reading Frame Cassette b into PmeI site of pBBV-Phas parent vector.

```
  1   ggccgcaaca gaggtggatg gacagacccg ttcttacacc ggactgggcg
 51   cgggatagga tattcagatt gggatgggat tgagcttaaa gccggcgctg
101   agaccatgct caaggtaggc aatgtcctca gcgtcgagcc cggcatctat
151   gtcgagggca ttggtggagc gcgcttcggg gataccgtgc ttgtaactga
201   gaccggatat gaggccctca ctccgcttga tcttggcaaa gatatttgac
251   gcatttatta gtatgtgtta attttcattt gcagtgcagt attttctatt
301   cgatctttat gtaattcgtt acaattaata aatattcaaa tcagattatt
351   gactgtcatt tgtatcaaat cgtgtttaat ggatatttttt attataatat
401   tgatgatatc tcaatcaaaa cgtagataat aataatattt atttaatatt
451   tttgcgtcgc acagtgaaaa tctatatgag attacaaaat accgacaaca
501   ttatttaaga tacatagaca ttaaccctga gactgttgga cagagctcat
551   tggtacctca gatctgggta actggcctaa ctggccttgg aggagctggc
601   aactcaaaat cccttttgcca aaaaccaaca tcatgccatc caccatgctt
651   gtatccagct gcgcgcaatg taccccgggc tgtgtatccc aaagcctcat
701   gcaacctaac agatggatcg tttggaaggc ctataacagc aaccacagac
```

```
 751   ttaaaacctt gcgcctccat agacttaagc aaatgtgtgt acaatgtgga
 801   tcctaggccc aacctttgat gcctatgtga cacgtaaaca gtactctcaa
 851   ctgtccaatc gtaagcgttc ctagccttcc agggcccagc gtaagcaata
 901   ccagccacaa cccctcaac ctcagcaacc aaccaagggt atctatcttg
 951   caacctctct agatcatcaa tccactcttg tggtgtttgt ggctctgtcc
1001   taaagttcac tgtagacgtc tcaatgtaat ggttaacgat atcacaaacc
1051   gcggccatat cagctgctgt agctggccta atctcaactg gtctcctctc
1101   cggagaagcc atggtttgga tccacaaact tacaaatttc tctgaagttg
1151   tatcctcagt acttcaaaga aaatagctta caccaatttt ttcttgtttt
1201   cacaaatgcc gaacttggtt cctatatag gaaaactcaa gggcaaaaat
1251   gacacggaaa aatataaaag gataagtagt gggggataag attcctttgt
1301   gataaggtta ctttccgccc ttacatttc caccttacat gtgtcctcta
1351   tgtctctttc acaatcaccg accttatctt cttcttttca ttgttgtcgt
1401   cagtgcttac gtcttcaaga ttcttttctt cgcctggttc ttcttttca
1451   atttctacgt attcttcttc gtattctggc agtataggat cttgtatctg
1501   tacattcttc attttgaac ataggttgca tatgtgccgc atattgatct
1551   gcttcttgct gagctcacat aatacttcca tagtttttcc cgtaaacatt
1601   ggattcttga tgctacatct tggataatta ccttctggcc ggccgcgaat
1651   tcgttggtag ggtgctagga aacttgtttt tggggttttg tataagggtt
1701   gaaacatccc tgaagtgtct cattttattt tatttattct ttgctgataa
1751   aaaaataaaa taaagaagc taagcacacg gtcaaccatt gctctactgc
1801   taaaggggtt atgtgtagtg ttttactgca taaattatgc agcaaacaag
1851   acaactcaaa ttaaaaaatt cctttgctt gtttttttgt tgtctctgac
1901   ttgactttct tgtggaagtt ggttgtataa ggattgggac accattgtcc
1951   ttataattta attttattct ttgctgataa aaaaaaaaa tttcatata
2001   gtgttaaata ataatttgtt aaataaccaa aaagtcaaat atgtttactc
2051   tcgtttaaat aattgagatt cgttccagca aggctaaacg attgtataga
2101   tttatgacaa tatttacttt tttatagata aatgttatat tataataaat
2151   ttatatacat atattatatg ttatttatta tttattatta ttttaaatcc
2201   ttcaatattt tatcaaacca actcataatt ttttttttat ctgtaagaag
2251   caataaaatt aaatagaccc actttaagga tgatccaacc tttatacaga
2301   gtaagagagt tcaaatagta cctttttcata tacatatcaa ctaaaatatt
2351   agaaatatca tggatcaaac cttataaaga cattaaataa gtggataagt
2401   ataatatata aatgggtagt atataatata taaatggata caaacttctc
2451   tctttataat tgttatgtct ccttaacatc ctaatataat acataagtgg
2501   gtaatatata atatataaat ggagacaaac ttcttccatt ataattgtta
2551   tgtcttctta acacttatgt ctcgttcaca atgctaaagt tagaattgtt
2601   tagaaagtct tatagtacac atttgttttt gtactatttg aagcattcca
2651   taagccgtca cgattcagat gatttataat aataagagga aatttatcat
```

| | |
|---|---|
| 2701 | agaacaataa ggtgcataga tagagtgtta atatatcata acatcctttg |
| 2751 | tttattcata gaagaagtga gatggagctc agttattata ctgttacatg |
| 2801 | gtcggataca atattccatg ctctccatga gctcttacac ctacatgcat |
| 2851 | tttagttcat actggtgacc ctcgaggcga tcgctttggc cggccattta |
| 2901 | aatggcgcgc ctttgcccgg gctttcctgc agggtttATC AACCACTTTG |
| 2951 | TACAAGAAAG CTGAACGAGA ACGTAAAAT GATATAAATA TCAATATATT |
| 3010 | AAATTAGATT TTGCATAAAA AACAGACTAC ATAATACTGT AAAACACAAC |
| 3051 | ATATCCAGTC ACTATGGTCG ACCTGCAGAC TGGCTGTGTA TAAGGGAGCC |
| 3101 | TGACATTTAT ATTCCCCAGA ACATCAGGTT AATGGCGTTT TTGATGTCAT |
| 3151 | TTTCGCGGTG GCTGAGATCA GCCACTTCTT CCCCGATAAC GGAGACCGGC |
| 3201 | ACACTGGCCA TATCGGTGGT CATCATGCGC CAGCTTTCAT CCCCGATATG |
| 3251 | CACCACCGGG TAAAGTTCAC GGGAGACTTT ATCTGACAGC AGACGTGCAC |
| 3301 | TGGCCAGGGG GATCACCATC CGTCGCCCGG GCGTGTCAAT AATATCACTC |
| 3351 | TGTACATCCA CAAACAGACG ATAACGGCTC TCTCTTTTAT AGGTGTAAAC |
| 3401 | CTTAAACTGC ATTTCACCAG TCCCTGTTCT CGTCAGCAAA AGAGCCGTTC |
| 3451 | ATTTCAATAA ACCGGGCGAC CTCAGCCATC CCTTCCTGAT TTTCCGCTTT |
| 3501 | CCAGCGTTCG GCACGCAGAC GACGGGCTTC ATTCTGCATG GTTGTGCTTA |
| 3551 | CCAGACCGGA GATATTGACA TCATATATGC CTTGAGCAAC TGATAGCTGT |
| 3601 | CGCTGTCAAC TGTCACTGTA ATACGCTGCT TCATAGCACA CCTCTTTTTG |
| 3651 | ACATACTTCG GGTATACATA TCAGTATATA TTCTTATACC GCAAAAATCA |
| 3701 | GCGCGCAAAT ACGCATACTG TTATCTGGCT TTTAGTAAGC CGGATCCAGA |
| 3751 | TCTTTACGCC CCGCCCTGCC ACTCATCGCA GTACTGTTGT AATTCATTAA |
| 3801 | GCATTCTGCC GACATGGAAG CCATCACAGA CGGCATGATG AACCTGAATC |
| 3851 | GCCAGCGGCA TCAGCACCTT GTCGCCTTGC GTATAATATT TGCCCATGGT |
| 3901 | GAAAACGGGG GCGAAGAAGT TGTCCATATT GGCCACGTTT AAATCAAAAC |
| 3951 | TGGTGAAACT CACCCAGGGA TTGGCTGAGA CGAAAAACAT ATTCTCAATA |
| 4001 | AACCCTTTAG GGAAATAGGC CAGGTTTTCA CCGTAACACG CCACATCTTG |
| 4051 | CGAATATATG TGTAGAAACT GCCGGAAATC GTCGTGGTAT TCACTCCAGA |
| 4101 | GCGATGAAAC GTTTCAGTTT GCTCATGGAA AACGGTGTAA CAAGGGTGA |
| 4151 | ACACTATCCC ATATCACCAG CTCACCGTCT TTCATTGCCA TACGGAATTC |
| 4201 | CGGATGAGCA TTCATCAGGC GGGCAAGAAT GTGAATAAGG CCGGATAAA |
| 4251 | ACTTGTGCTT ATTTTTCTTT ACGGTCTTTA AAAAGGCCGT AATATCCAGC |
| 4301 | TGAACGGTCT GGTTATAGGT ACATTGAGCA ACTGACTGAA ATGCCTCAAA |
| 4351 | ATGTTCTTTA CGATGCCATT GGGATATATC AACGGTGGTA TATCCAGTGA |
| 4401 | TTTTTTTCTC CATTTTAGCT TCCTTAGCTC CTGAAAATCT CGCCGGATCC |
| 4451 | TAACTCAAAA TCCACACATT ATACGAGCCG GAAGCATAAA GTGTAAAGCC |
| 4501 | TGGGGTGCCT AATGCGGCCG CCATAGTGAC TGGATATGTT GTGTTTTACA |
| 4551 | GTATTATGTA GTCTGTTTTT TATGCAAAAT CTAATTTAAT ATATTGATAT |
| 4601 | TTATATCATT TTACGTTTCT CGTTCAGCTT TTTTGTACAA ACTTGTTGAT |
| 4651 | aaacttaatt aaggatccta gagtagtatt gaatatgagt tgggttgggg |

```
4701  tattatagta gtagagtagt agtactctgg atggatggat gatgaaagaa
4751  gtgagtgata ttagaggtat ttataggtat tatataagag agaaggtggt
4801  tggaacatgc atggagattt gggcatggga tgacacgcat atgcaggttg
4851  acgtgtgttg aagtgaagaa attgaggtgg cggaagagaa tgaatatata
4901  caggtggttg tggtgatgat gaagaaaaag gcaatgtgtt tgtgtgtggg
4951  ttgagatggg tgagccattt aaagtgcatg ttaagcacgt gttgctttgc
5001  atggcattta gacatacatg gacgcggcga tcttgatcag ccagtgacta
5051  atttgagttg gttgtgtgat tgcgttttgt ctctctgttt tgtcttttt
5101  ctttgttctt tgtctttttc ttgcgcaagc atccatgcat gaaccaaaag
5151  accacagagt gtcatggcaa cccacagtaa ttccagttac ggacttacat
5201  accaagaaaa ggtaaaagca ataagaaata tatgaaaatt agtccaccat
5251  aaatcttata gtttatggtt tagggtaaca ctctaacact ctactacatt
5301  acttatattt actttaaact atctataaaa caatttaaac atagtagaat
5351  aataaatcaa tagtcacaaa ttcaacaatt aaacttaaaa ttaaaaaagt
5401  aatattttaa ttatatctaa ttaatttttt agaagtaata ttgagtattt
5451  gatatatgaa atcttgaata tagtaactat tattaaaatt actttagaag
5501  atgtgtctcg catgtaaaag cagatcttca gttacttccg tagtgtcaaa
5551  tgggaattat agaattttgc ataacatgac ttgcttcaga ataccacaa
5601  atcattgttt ggtgaaattt tcattgtata aaaaaatac aatgataatt
5651  ggattattta ttcaaagaaa aaatggcta gttgtgtcac tgggtgttg
5701  ctttaagatc agtcgaataa aaaaattatg gagttaaatt ttattacttt
5751  tgaaacaact tattattatg agatttacgt ggttgaaaaa tatttgataa
5801  atatatttt aaaatataaa atgggaaatc cttcttaagg taagaatt
5851  gtttatattg tatattaaac atttatatga agaagaataa gaataaatca
5901  ttatgctttc taccaacgct aaaattaagt aaattatata tttcaatatg
5951  aaaatgttag actacattaa agatagacgg gacttcataa aattttatgc
6001  ggtttgaaaa tgtttaacaa ataataaatt tgtagggata tcgtgtgcgg
6051  aagcgtgata atttcaacca aagattatga gaaattaaag taacaagtaa
6101  agtgagaatg ataccagaat ttttaggtgg aaaacccctt taaatagagg
6151  taaaaaacca ccggcgagag agccaaaact ttcactataa tgatactggg
6201  agtacaatgg cggccggggc tgcaattgat ccggtgagta atattgtacg
6251  gctaagagcg aatttggcct gtagacctca attgcgagct ttctaatttc
6301  aaactattcg ggcctaactt ttggtgtgat gatgctgact ggcaggatat
6351  ataccgttgt aatttgagct cgtgtgaata agtcgctgtg tatgtttgtt
6401  tgattgtttc tgttggagtg cagcccattt caccggacaa gtcggctaga
6451  ttgatttagc cctgatgaac tgccgagggg aagccatctt gagcgcggaa
6501  tgggaatgga tcgaaccggg agcacaggat gacgcctaac aattcattca
6551  agccgacacc gcttcgcggc gcggcttaat tcaggagtta acatcatga
6601  gggaagcggt gatcgccgaa gtatcgactc aactatcaga ggtagttggc
```

-continued

| | |
|---|---|
| 6651 | gtcatcgagc gccatctcga accgacgttg ctggccgtac atttgtacgg |
| 6701 | ctccgcagtg gatggcggcc tgaagccaca cagtgatatt gatttgctgg |
| 6751 | ttacggtgac cgtaaggctt gatgaaacaa cgcggcgagc tttgatcaac |
| 6801 | gacctttggg aaacttcggc ttcccctgga gagagcgaga ttctccgcgc |
| 6851 | tgtagaagtc accattgttg tgcacgacga catcattccg tggcgttatc |
| 6901 | cagctaagcg cgaactgcaa tttggagaat ggcagcgcaa tgacattctt |
| 6951 | gcaggtatct tcgagccagc cacgatcgac attgatctgg ctatcttgct |
| 7001 | gacaaaagca agagaacata gcgttgcctt ggtaggtcca gcggcggagg |
| 7051 | aactctttga tccggttcct gaacaggatc tatttgaggc gctaaatgaa |
| 7101 | accttaacgc tatggaactc gccgcccgac tgggctggcg atgagcgaaa |
| 7151 | tgtagtgctt acgttgtccc gcatttggta cagcgcagta accggcaaaa |
| 7201 | tcgcgccgaa ggatgtcgct gccgactggg caatggagcg cctgccggcc |
| 7251 | cagtatcagc ccgtcatact tgaagctagg caggcttatc ttggacaaga |
| 7301 | agatcgcttg gcctcgcgcg cagatcagtt ggaagaattt gttcactacg |
| 7351 | tgaaaggcga gatcaccaag gtagtcggca aataatgtct aacaattcgt |
| 7401 | tcaagccgac gccgcttcgc ggcgcggctt aactcaagcg ttagagagct |
| 7451 | ggggaagact atgcgcgatc tgttgaaggt ggttctaagc ctcgtacttg |
| 7501 | cgatggcatt tcgatcgaaa ggggtacaaa ttcccactaa gcgctcgggg |
| 7551 | gctgagaaag cccagtaagg aaacaactgt aggttcgagt cgcgagatcc |
| 7601 | cccggaacca aggaagtag gttaaacccg ctccgatcag gccgagccac |
| 7651 | gccaggccga gaacattggt tcctgtaggc atcgggattg gcggatcaaa |
| 7701 | cactaaagct actggaacga gcagaagtcc tccggccgcc agttgccagg |
| 7751 | ccgtaaaggt gagcagaggc acgggaggtt gccacttgcg ggtcagcacg |
| 7801 | gttccgaacg ccatggaaac cgccccgcc aggcccgctg cgacgccgac |
| 7851 | aggatctagc gctgcgtttg gtgtcaacac caacagcgcc acgcccgcag |
| 7901 | ttccgcaaat agcccccagg accgccatca atcgtatcgg gctacctagc |
| 7951 | agagcggcag agatgaacac gaccatcagc ggctgcacag cgcctaccgt |
| 8001 | cgccgcgacc cgcccggcag gcggtagacc gaaataaaca acaagctcca |
| 8051 | gaatagcgaa atattaagtg cgccgaggat gaagatgcgc atccaccaga |
| 8101 | ttcccgttgg aatctgtcgg acgatcatca cgagcaataa acccgccggc |
| 8151 | aacgcccgca gcagcatacc ggcgacccct cggcctcgct gttcgggctc |
| 8201 | cacgaaaacg ccggacagat gcgccttgtg agcgtccttg ggccgtcct |
| 8251 | cctgtttgaa gaccgacagc ccaatgatct cgccgtcgat gtaggcgccg |
| 8301 | aatgccacgg catctcgcaa ccgttcagcg aacgcctcca tgggcttttt |
| 8351 | ctcctcgtgc tcgtaaacgg acccgaacat ctctggagct tcttcaggg |
| 8401 | ccgacaatcg gatctcgcgg aaatcctgca cgtcggccgc tccaagccgt |
| 8451 | cgaatctgag ccttaatcac aattgtcaat tttaatcctc tgtttatcgg |
| 8501 | cagttcgtag agcgcgccgt gcgcccgagc gatactgagc gaagcaagtg |
| 8551 | cgtcgagcag tgcccgcttg ttcctgaaat gccagtaaag cgctggctgc |
| 8601 | tgaaccccca gccggaactg accccacaag gccctagcgt ttgcaatgca |

```
     8651  ccaggtcatc attgacccag gcgtgttcca ccaggccgct gcctcgcaac
     8701  tcttcgcagg cttcgccgac ctgctcgcgc cacttcttca cgcgggtgga
     8751  atccgatccg cacatgaggc ggaaggtttc cagcttgagc gggtacggct
     8801  cccggtgcga gctgaaatag tcgaacatcc gtcgggccgt cggcgacagc
     8851  ttgcggtact ctcccatat gaatttcgtg tagtggtcgc cagcaaacag
     8901  cacgacgatt tcctcgtcga tcaggacctg gcaacgggac gttttcttgc
     8951  cacggtccag gacgcggaag cggtgcagca gcgacaccga ttccaggtgc
     9001  ccaacgcggt cggacgtgaa gcccatcgcc gtcgcctgta ggcgcgacag
     9051  gcattcctcg gccttcgtgt aataccggcc attgatcgac cagcccaggt
     9101  cctggcaaag ctcgtagaac gtgaaggtga tcggctcgcc gatagggtg
     9151  cgcttcgcgt actccaacac ctgctgccac accagttcgt catcgtcggc
     9201  ccgcagctcg acgccggtgt aggtgatctt cacgtccttg ttgacgtgga
     9251  aaatgacctt gttttgcagc gcctcgcgcg ggattttctt gttgcgcgtg
     9301  gtgaacaggg cagagcgggc cgtgtcgttt ggcatcgctc gcatcgtgtc
     9351  cggccacggc gcaatatcga acaaggaaag ctgcatttcc ttgatctgct
     9401  gcttcgtgtg tttcagcaac gcggcctgct tggcctcgct gacctgtttt
     9451  gccaggtcct cgccggcggt ttttcgcttc ttggtcgtca tagttcctcg
     9501  cgtgtcgatg gtcatcgact tcgccaaacc tgccgcctcc tgttcgagac
     9551  gacgcgaacg ctccacggcg gccgatggcg cgggcagggc aggggagcc
     9601  agttgcacgc tgtcgcgctc gatcttggcc gtagcttgct ggaccatcga
     9651  gccgacggac tggaaggttt cgcggggcgc acgcatgacg gtgcggcttg
     9701  cgatggtttc ggcatcctcg gcggaaaacc ccgcgtcgat cagttcttgc
     9751  ctgtatgcct tccggtcaaa cgtccgattc attcaccctc cttgcgggat
     9801  tgccccgact cacgccgggg caatgtgccc ttattcctga tttgacccgc
     9851  ctggtgcctt ggtgtccaga taatccacct tatcggcaat gaagtcggtc
     9901  ccgtagaccg tctggccgtc cttctcgtac ttggtattcc gaatcttgcc
     9951  ctgcacgaat accagcgacc ccttgcccaa atacttgccg tgggcctcgg
    10001  cctgagagcc aaaacacttg atgcggaaga agtcggtgcg ctcctgcttg
    10051  tcgccggcat cgttgcgcca ctcttcatta accgctatat cgaaaattgc
    10101  ttgcggcttg ttagaattgc catgacgtac ctcggtgtca cgggtaagat
    10151  taccgataaa ctggaactga ttatggcnnc tcgaaattcc ctcggtcttg
    10201  ccttgctcgt cggtgatgta cttcaccagc tccgcgaagt cgctcttctt
    10251  gatggagcgc atgggacgt gcttggcaat cacgcgcacc ccccggccgt
    10301  tttagcggct aaaaaagtca tggctctgcc ctcgggcgga ccacgcccat
    10351  catgaccttg ccaagctcgt cctgcttctc ttcgatcttc gccagcaggg
    10401  cgaggatcgt ggcatcaccg aaccgcgcc tgcgcgggtc gtcggtgagc
    10451  cagagtttca gcaggccgcc caggcggccc aggtcgccat tgatgcgggc
    10501  cagctcgcgg acgtgctcat agtccacgac gcccgtgatt ttgtagccct
    10551  ggccgacggc cagcaggtag gccgacaggc tcatgccggc cgccgccgcc
```

-continued

```
10601  ttttcctcaa tcgctcttcg ttcgtctgga aggcagtaca ccttgatagg
10651  tgggctgccc ttcctggttg gcttggtttc atcagccatc cgcttgccct
10701  catctgttac gccggcggta gccggccagc ctcgcagagc aggattcccg
10751  ttgagcaccg ccaggtgcga ataagggaca gtgaagaagg aacacccgct
10801  cgcgggtggg cctacttcac ctatcctgcc cggctgacgc cgttggatac
10851  accaaggaaa gtctacacga accctttggc aaaatcctgt atatcgtgcg
10901  aaaaaggatg gatataccga aaaaatcgct ataatgaccc cgaagcaggg
10951  ttatgcagcg gaaaagatcc gtcgaccctt tccgacgctc accgggctgg
11001  ttgccctcgc cgctgggctg gcggccgtct atggccctgc aaacgcgcca
11051  gaaacgccgt cgaagccgtg tgcgagacac cgcggccgcc ggcgttgtgg
11101  ataccacgcg gaaaacttgg ccctcactga cagatgaggg gcggacgttg
11151  acacttgagg ggccgactca cccggcgcgg cgttgacaga tgaggggcag
11201  gctcgatttc ggccggcgac gtggagctga ccagcctcgc aaatcggcga
11251  aaacgcctga ttttacgcga gtttcccaca gatgatgtgg acaagcctgg
11301  ggataagtgc cctgcggtat tgacacttga ggggcgcgac tactgacaga
11351  tgaggggcgc gatccttgac acttgagggg cagagtgatg acagatgagg
11401  ggcgcaccta ttgacatttg aggggctgtc cacaggcaga aaatccagca
11451  tttgcaaggg tttccgcccg ttttttcggcc accgctaacc tgtcttttaa
11501  cctgctttta aaccaatatt tataaacctt gtttttaacc agggctgcgc
11551  cctggcgcgt gaccgcgcac gccgaagggg ggtgcccccc cttctcgaac
11601  cctcccggcc cgctaacgcg ggcctcccat cccccccaggg gctgcgcccc
11651  tcggccgcga acggcctcac cccaaaaatg gcaggccaag cttgcttggt
11701  cgttccggta cgtaccgtga acgtcggctc gattgtacct gcgttcaaat
11751  actttgcgat cgtgttgcgc gcctgcccgg tgcgtcggct gatctgcgg
11801  atcgactgct tctctcgcaa cgccatccga cggatgatgt ttaaaagtcc
11851  catgtggatc actccgttgc cccgtcgctc accgtgttgg ggggaaggtg
11901  cacatggctc agttctcaat ggaaattatc tgcctaaccg gctcagttct
11951  gcgtagaaac caacatgcaa gctccaccgg gtgcaaagcg gcagcggcgg
12001  caggatatat tcaattgtaa atggcttcat gtccgggaaa tctacatgga
12051  tcagcaatga gtatgatggt caatatggag aaaaagaaaag agtaattacc
12101  aattttttt caattcaaaa atgtagatgt ccgcagcgtt attataaaat
12151  gaaagtacat tttgataaaa cgacaaatta cgatccgtcg tatttatagg
12201  cgaaagcaat aaacaaatta ttctaattcg gaaatctttta tttcgacgtg
12251  tctacattca cgtccaaatg ggggcggcga att
```

After *Agrobacterium* transformation the presence of the construct was confirmed by PCR. Finally, a mixture of 3 independent *Agrobacterium* transformation events were used for transformation into *Arabidopsis*.

Results of F-box Overexpression

Lines that have positive increase in oil content have been taken to T3 and/or T4 generation and reanalyzed.

Figure 2:
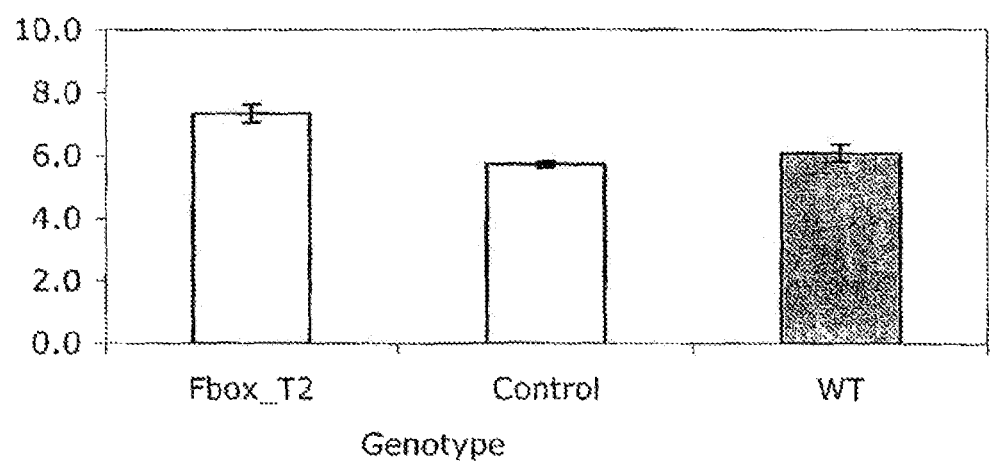
FIG. 2 is a graphical representation of experiments demonstrating total seed FAMEs of F-box transgenic lines compared to WT, and vector control lines. Error bars are SE based on 18 lines: 3 duplicate for each line.
Figure 3:
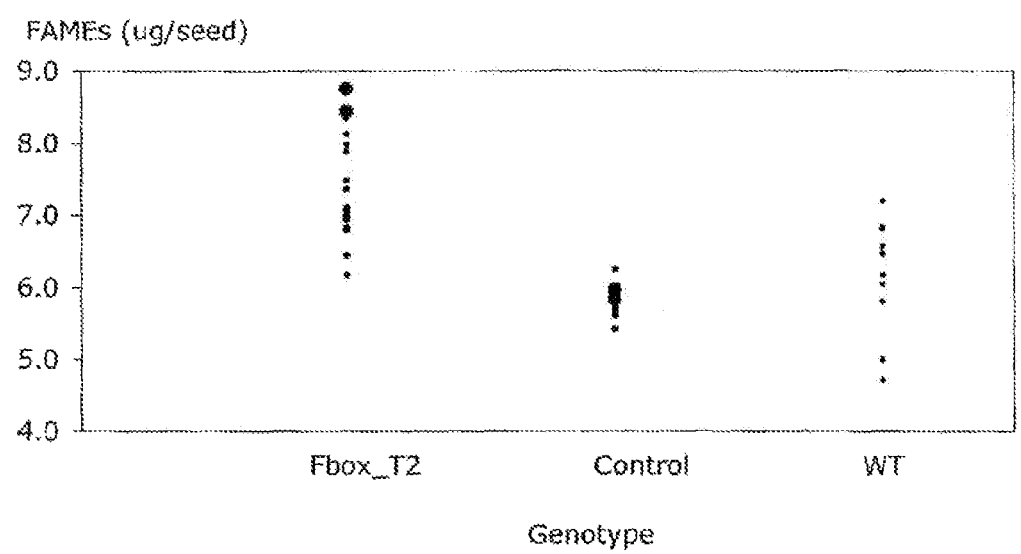
FIG. 3 is a graphical representation of experiments demonstrating total seed FAMEs of transgenic lines versus WT and vector control lines. Large dots are the two lines with highest oil content and were named Fbox2 and Fbox3 later chosen for next generation analysis.
Figure 4:
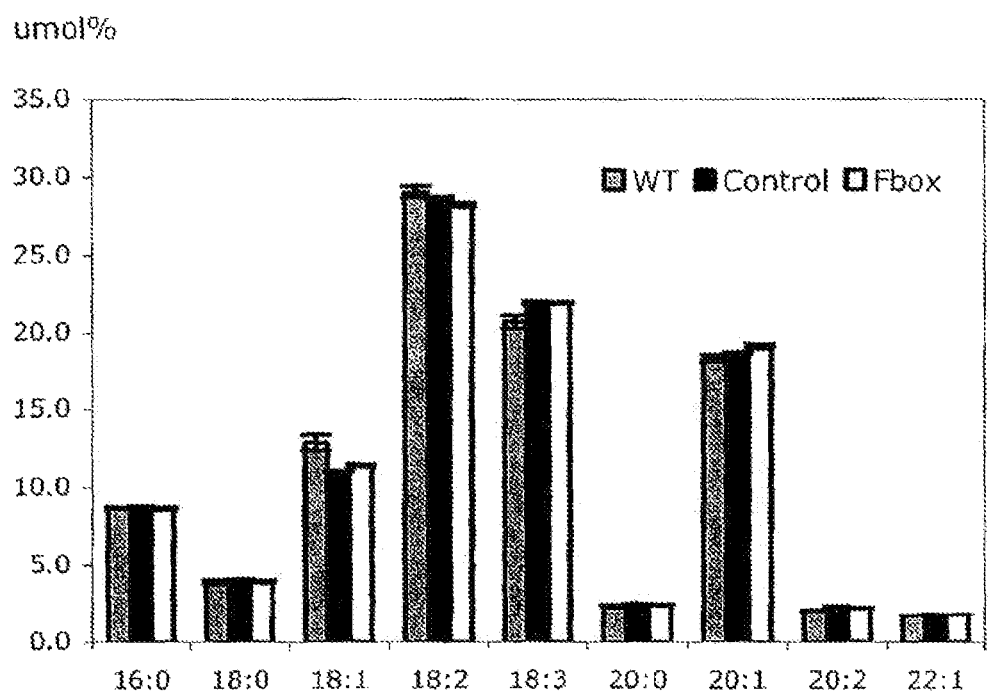
FIG. 4 is a graphical representation of experiments showing the fatty acid profile and fatty acid molar ratio composition of F-box transgenic lines versus control plants.
Figure 5:
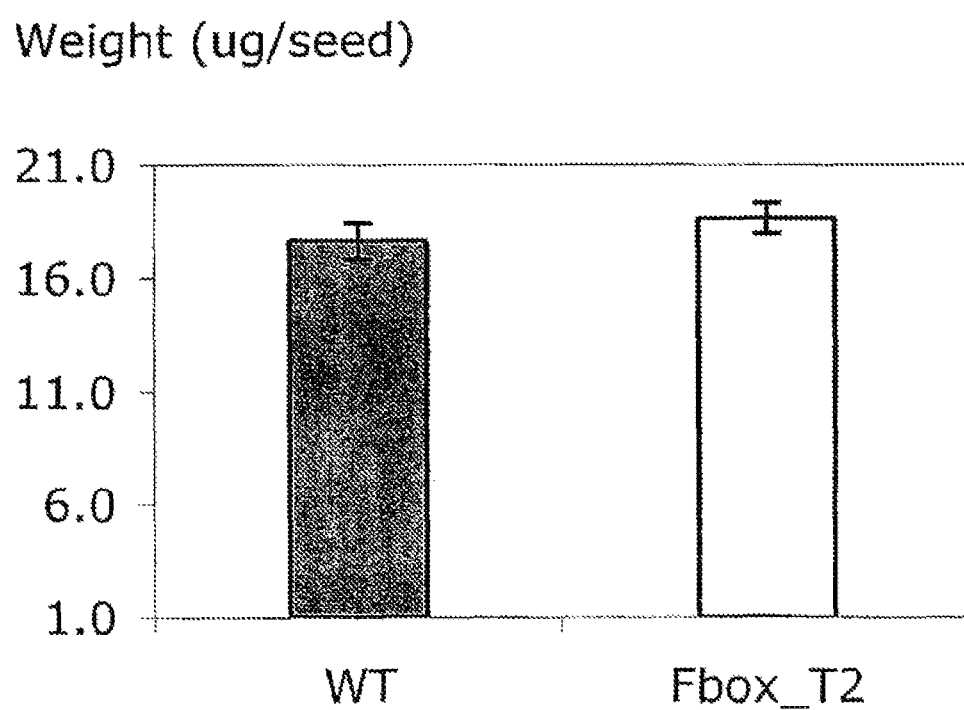
FIG. 5 is a graphical representation of seed weight determination. Around 400 seeds were counted for both wild type seeds and transformants with F-box genes. Counted seeds were stored in a desiccator overnight then determined using an analytical balance. Error bars are SE based on 6 replicates.
Figure 6:
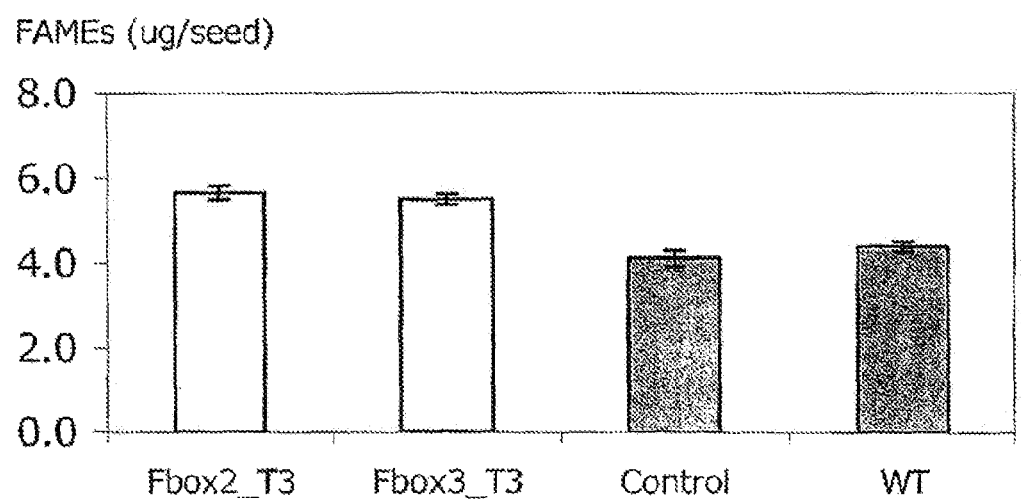
FIG. 6 is a graphical representation of experiments demonstrating total FAMEs per seed in F-box T3 seeds versus WT and vector control lines. The error bars are SE based on data obtained from 12 plants for F-box2 and F-box3 lines; 6 plants for WT and vector control lines. The two lines here named F-box2 and F-box3 are the two data points indicated by large dots in FIG. 3.
Figure 7:
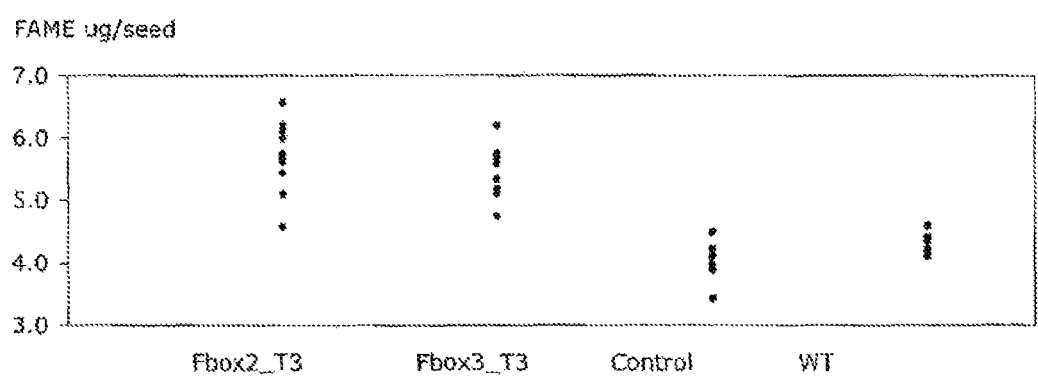
FIG. 7 is a graphical representation of experiments demonstrating total seed FAMEs of transgenic lines (F-box2 and F-box3) versus WT and vector control lines.

Screening has shown that over expression of F-box (At3g06240), when driven under a seed specific promoter phaseolin, produced seeds with higher oil phenotype is shown in FIGS. 1-5. Also the data obtained for the next (T3) generation is shown in FIGS. 6-7, and further analysis of other aspects of the transgenic seeds is shown in FIG. 8-9. In particular, FIG. 1 shows the oil content of transgenic phaseolin-F-box lines compared with vector control lines. Data shown are average of 18 lines (T2) and error bars are SE. FIG. 2 shows the total seed FAMEs of F-box transgenic lines compared to WT, and vector control lines (error bars are SE based on 18 lines: 3 duplicate for each line). FIG. 3 shows the total seed FAMEs of transgenic lines versus WT and vector control lines (large dots are the two lines with highest oil content and were named F-box2 and F-box3 later chosen for next generation analysis). FIG. 4 shows the fatty acid profile and fatty acid molar ratio composition of F-box transgenic lines versus control plants. FIG. 5 shows the seed weight determination (around 400 seeds were counted for both wild type seeds and transformants with F-box genes and counted seeds were stored in desiccators overnight, and then determined using an analytical balance and error bars are SE based on 6 replicates).

Data in above section show that there is an >10% increase in oil content in F-box overexpressor lines comparing to wild type plants. This increase is confirmed both at a per mg basis and at a per seed basis. To further confirm this result, it is essential to determine changes in oil content for next generation. Furthermore, there is a small yet significant decrease in 18:1 and 18:2 in F-box overexpressors comparing to wild type, and there is a significant increase in 18:3 observed. The reason for this is not yet clear.

Evaluation of F-box gene at T3 generation: T2 plants from F-box2 and F-box3 lines (see FIG. 3) were grown under standard conditions. To eliminate the potential effect of BASTA on seed metabolism, transformants were screened by PCR rather than by BASTA spray. F-box2 and F-box3 lines were grown together with WT and vector control lines. FAME analysis of T3 seeds was shown in FIG. 6.

FIG. 6 shows the total FAMEs per seed in F-box T3 seeds versus WT and vector control lines (the error bars are SE based on data obtained from 12 plants for F-box2 and F-box3 lines; 6 plants for WT and vector control lines; and the two lines here named F-box2 and F-box3 are the two data points indicated by big dots in FIG. 3). FIG. 7 shows the total seed FAMEs of transgenic lines (F-box2 and F-box3) versus WT and vector control lines.

Figure 8A:
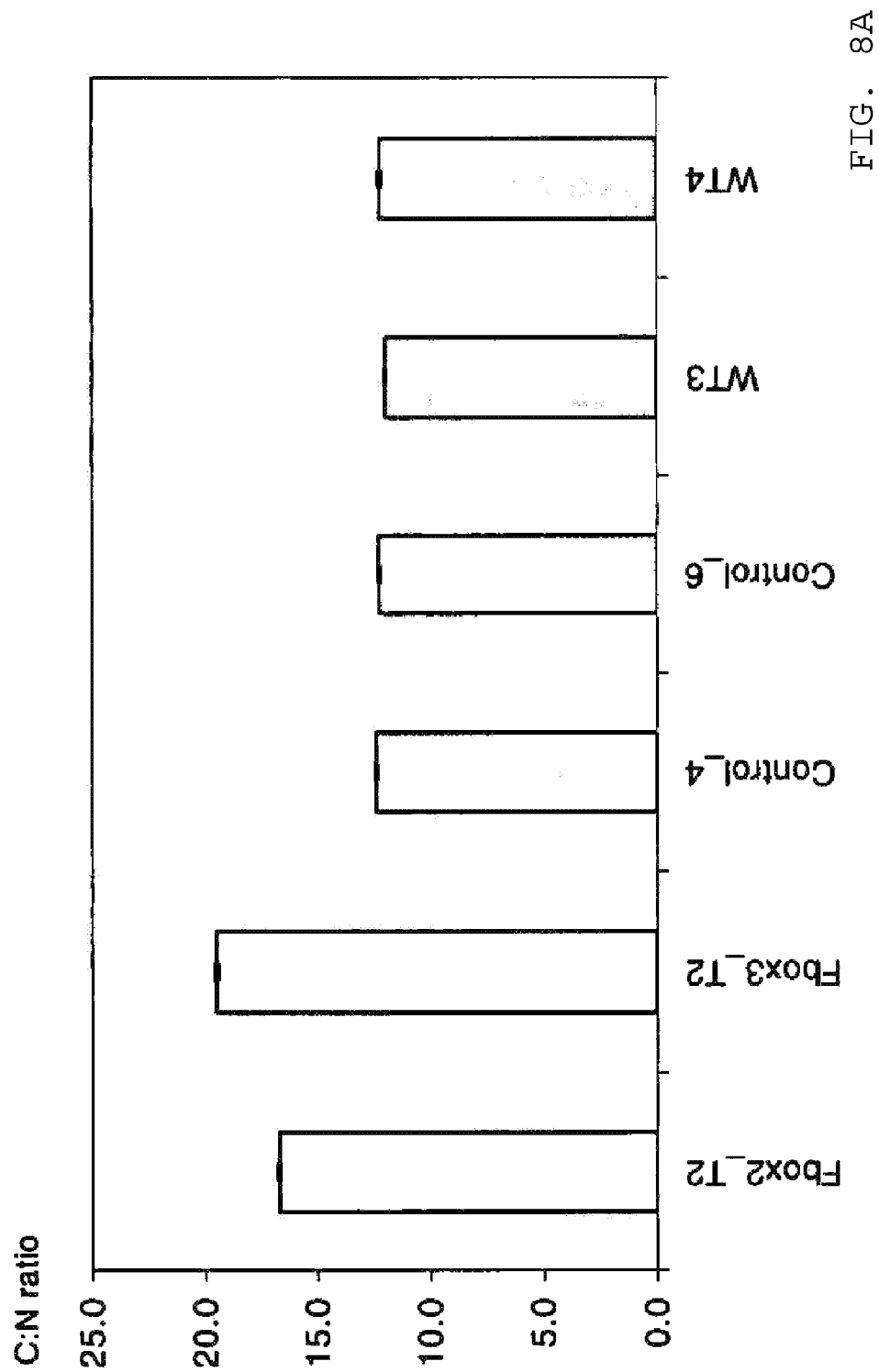
FIG. 8(A) is a graphical representation of experiments demonstrating a C:N ratio analysis for two independent lines F-box2 and F-box3. Error bars are SE based on six replicates.
Figure 8B:
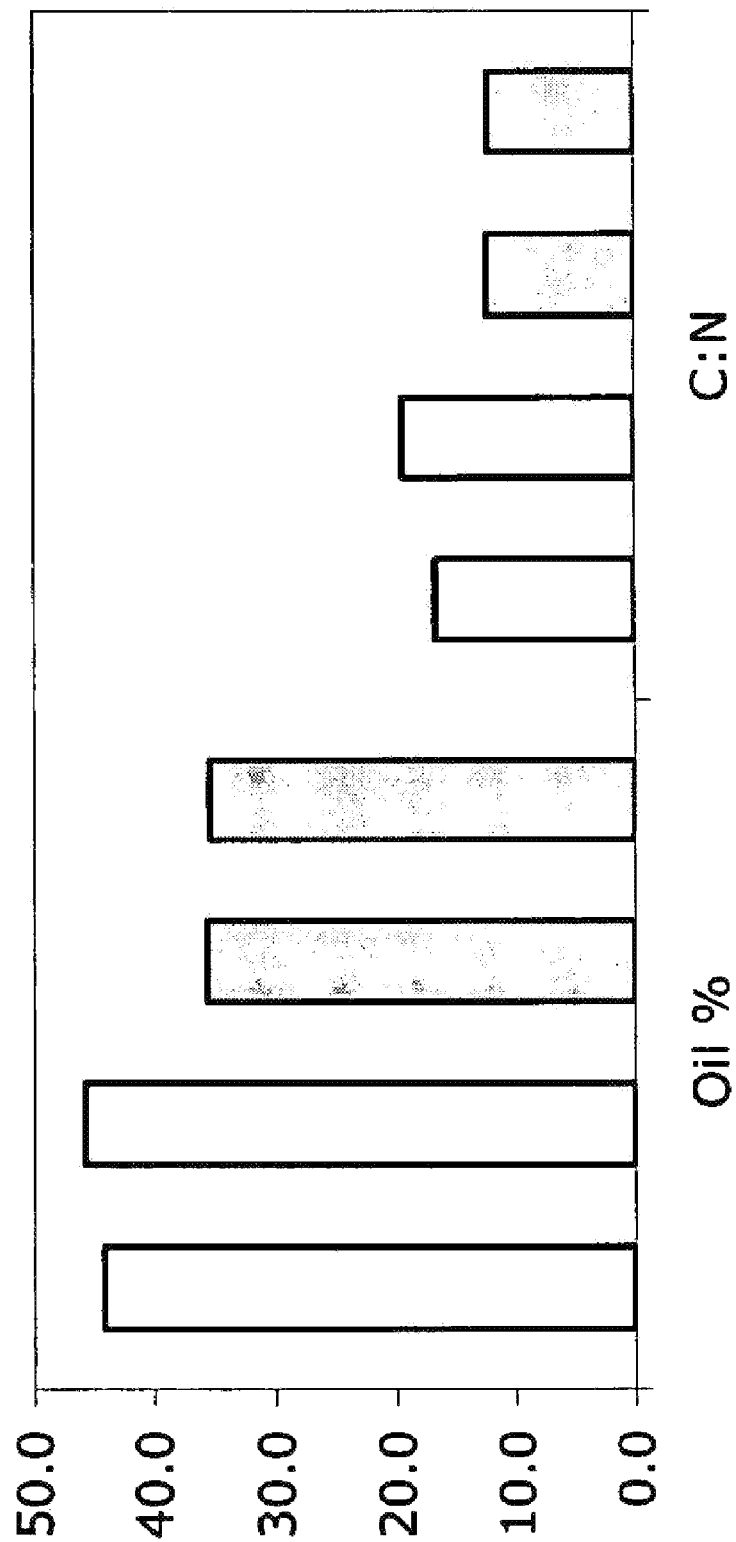
FIG. 8(B) is a graphical representation of experiments demonstrating the positive correlation between oil content and C:N ratio. Open columns are overexpressors F-box2 and F-box3; grey columns are Wild type *Arabidopsis* seeds.

C:N ratio analysis of T2 seeds: The two lines F-box2 and F-box3 were chosen for C:N ratio analysis. This analysis will confirm the changes the seed storage compounds (oil versus protein) (see FIG. 8). FIG. 8(a) shows the C:N ratio analysis for two independent lines F-box2 and F-box3. Error bars are SE based on six replicates. FIG. 8(b) shows the positive correlation between oil content and C:N ratio further that confirms the result (open columns are overexpressors F-box2 and F-box3; grey columns are Wild type *Arabidopsis* seeds).

Results of F-Box Knock-Out

KO (knock-out) analysis of F-box gene: Salk T-DNA insertion lines (SALK_048969 and SALK_048962) were ordered, and homozygous plants were picked up by PCR from line SALK_048969, which has a T-DNA insertion at the last exon of the gene. Homozygous plants together with WT plants were grown to maturity; seeds were analyzed for total FAMEs (see FIG. 9).

Figure 9A:
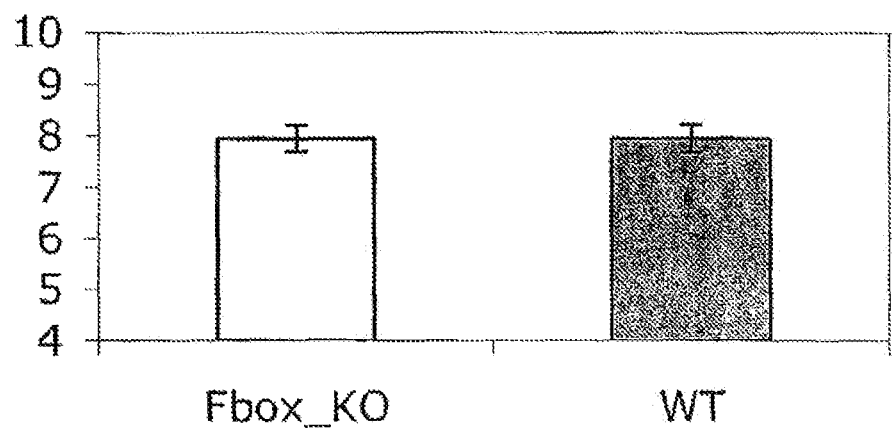
FIG. 9(A) is a graphical representation of experiments demonstrating a FAME analysis of F-box-KO lines.
Figure 9B:
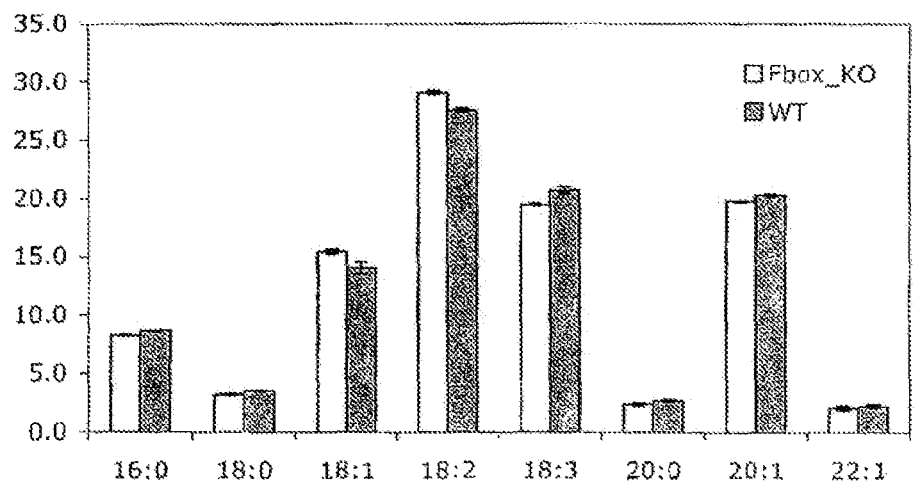
FIG. 9(B) is a graphical representation of experiments demonstrating a fatty acid profile of KO lines and WT. Error bars are SE based on nine independent replicates.
Figure 12:
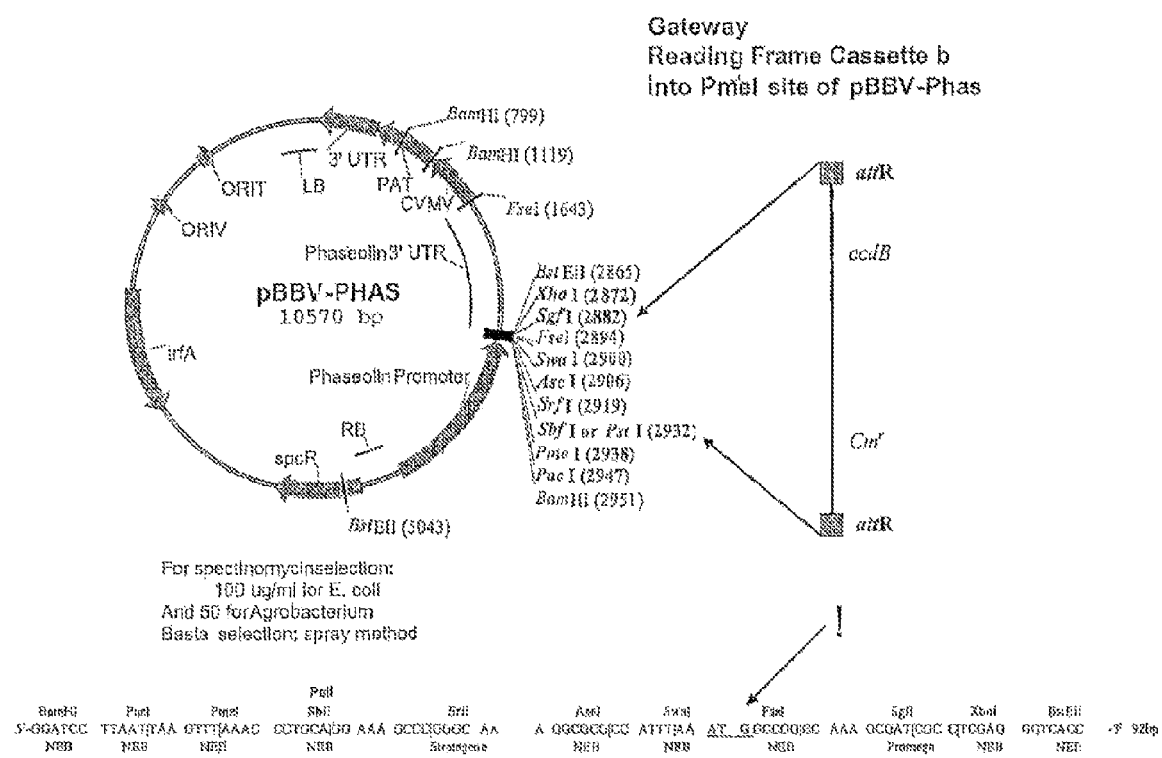
FIG. 12 is a diagrammatic representation of the seed-specific pGATE-PHASE: F-box vector showing the site of cloning behing the seed-specific phaseolin promoter.

FIG. 9(a) shows the FAME analysis of F-box-KO lines, and FIG. 9(b) shows the fatty acid profile of KO lines and WT (error bars are SE based on nine independent replicates). As shown above, there were no observable differences in oil content between WT and F-box_KO line; however there was a significant increase in 18:1 and 18:2 in F-box_KO comparing to wild type, and there was a significant decrease in 18:3 observed. This mirrors the profile observed with the overexpression lines (See FIG. 4).

Therefore, through this detailed analysis of F-box transgenic lines, it has been shown that overexpression of an F-box gene in *Arabidopsis* can increase total oil content by more than 10%. Indeed, this increase was confirmed in two generations and the analysis was validated with two different approaches (total FAMEs and C:N ratio analysis).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A genetic construct comprising the nucleic acid sequence of SEQ ID NO:2 operably linked to a heterologous seed-specific promoter that can drive expression of the F-box protein encoded by the nucleic acid sequence, wherein expression of said F-box protein encoded by said nucleic acid sequence increases seed oil content of a plant by at least 10% as compared to a wild type plant seed of the same species.

2. The genetic construct of claim 1, wherein said seed-specific promoter is a phaseolin promoter.

3. The genetic construct of claim 1, wherein the genetic construct comprises a pBBV-PHAS expression vector.

4. A transgenic plant comprising a nucleic acid sequence encoding an F-box protein having at least 95% sequence identity to SEQ ID NO:1, wherein the nucleic acid sequence is operably linked to a heterologous seed-specific promoter that can drive expression of said F-box protein encoded by the nucleic acid sequence, and wherein expression of said F-box protein encoded by said nucleic acid sequence increases seed oil content of the transgenic plant by at least 10% as compared to a wild type plant of the same species.

5. The transgenic plant of claim 4, wherein the plant is *Arabidopsis thaliana*.

6. The transgenic plant of claim 4, wherein the plant is selected from the group consisting of soybean, palm, rapeseed and sunflower.

7. A recombinant plant seed comprising a genetic construct comprising the nucleic acid sequence of SEQ ID NO:2 operably linked to a heterologous seed-specific promoter, wherein expression of the F-box protein encoded by the nucleic acid sequence increases the recombinant plant seed's oil content by at least 10% compared to a wild type plant seed of the same species.

8. The plant seed of claim 7, wherein said seed-specific promoter is a phaseolin promoter.

9. A recombinant plant seed comprising a genetic construct comprising a nucleic acid sequence encoding an F-box protein having at least 95% identity to SEQ ID NO:1, wherein the nucleic acid sequence is operably linked to a heterologous seed-specific promoter that can drive expression of said F-box protein encoded by the nucleic acid sequence, and wherein expression of said F-box protein encoded by said nucleic acid sequence increases seed oil content of the recombinant plant seed by at least 10% as compared to a wild type plant seed of the same species.

10. The plant seed of claim 7 or 9, selected from the group of seeds consisting of soybean, palm, rapeseed and sunflower seeds.

* * * * *

UNITED STATES PATENT AND TRADEMARK OFFICE
CERTIFICATE OF CORRECTION

PATENT NO. : 9,006,518 B2  
APPLICATION NO. : 13/039018  
DATED : April 14, 2015  
INVENTOR(S) : Ohlrogge et al.

Page 1 of 1

It is certified that error appears in the above-identified patent and that said Letters Patent is hereby corrected as shown below:

Claims

In column 61, line 35, in Claim 6, delete "sunflower." and insert --sunflower seeds.--, therefor Signed and Sealed this
Seventeenth Day of November, 2015

Michelle K. Lee
*Director of the United States Patent and Trademark Office*